(12) United States Patent
Krebs et al.

(10) Patent No.: US 7,595,173 B2
(45) Date of Patent: Sep. 29, 2009

(54) LOW-COST PRODUCTION OF PEPTIDES

(75) Inventors: Joseph F. Krebs, Austin, TX (US); Paul S. Zorner, Carlsbad, CA (US); Ian A. Tomlinson, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/971,444

(22) Filed: Oct. 22, 2004

(65) Prior Publication Data

US 2005/0227321 A1    Oct. 13, 2005

Related U.S. Application Data

(63) Continuation of application No. PCT/US03/12407, filed on Apr. 22, 2003.

(60) Provisional application No. 60/374,644, filed on Apr. 22, 2002.

(51) Int. Cl.
C12P 21/06 (2006.01)
C07H 21/04 (2006.01)
C07K 5/06 (2006.01)

(52) U.S. Cl. ................. 435/69.1; 435/252.34; 435/212; 435/471; 530/330; 530/331; 536/23.2

(58) Field of Classification Search ................ 435/69.1, 435/252.34, 212, 471; 530/330, 331; 536/23.2
See application file for complete search history.

(56) References Cited

U.S. PATENT DOCUMENTS

| | | | |
|---|---|---|---|
| 4,108,724 A | 8/1978 | Nara et al. | |
| 4,853,334 A | 8/1989 | Vandenbergh et al. | |
| 5,055,294 A | 10/1991 | Gilroy | |
| 5,128,130 A | 7/1992 | Gilroy et al. | |
| 5,169,760 A | 12/1992 | Wilcox | |
| 5,206,154 A | 4/1993 | Lai et al. | |
| 5,348,742 A | 9/1994 | Howell et al. | |
| 5,504,190 A | 4/1996 | Houghten et al. | |
| 5,506,120 A * | 4/1996 | Yamamoto et al. | 435/69.7 |
| 5,516,755 A | 5/1996 | Gulavita et al. | |
| 5,527,883 A | 6/1996 | Thompson et al. | |
| 5,593,866 A * | 1/1997 | Hancock et al. | 435/69.7 |
| 5,688,767 A | 11/1997 | Hancock et al. | |
| 5,707,855 A | 1/1998 | Hancock et al. | |
| 5,711,945 A | 1/1998 | Blanchette et al. | |
| 5,716,849 A | 2/1998 | Ligon et al. | |
| 5,789,377 A | 8/1998 | Hancock et al. | |
| 5,824,874 A | 10/1998 | Ulbrich et al. | |
| 5,840,554 A | 11/1998 | Thompson et al. | |
| 5,851,802 A * | 12/1998 | Better | 435/69.7 |
| 5,861,478 A | 1/1999 | Jaynes | |
| 5,891,851 A | 4/1999 | Vertesy et al. | |
| 5,962,410 A | 10/1999 | Jaynes et al. | |
| 5,985,617 A * | 11/1999 | Liao | 435/72 |
| 5,994,306 A | 11/1999 | Chang et al. | |
| 6,048,713 A | 4/2000 | Murakami et al. | |
| 6,071,879 A | 6/2000 | Pereira | |
| 6,132,775 A | 10/2000 | Elsbach et al. | |
| 6,183,992 B1 | 2/2001 | Kim et al. | |
| 6,242,219 B1 | 6/2001 | Better | |
| 6,255,279 B1 | 7/2001 | Christophers et al. | |
| 6,255,282 B1 | 7/2001 | Jaynes | |
| 6,274,344 B1 | 8/2001 | Better | |
| 6,303,568 B1 | 10/2001 | Jaynes et al. | |
| 6,316,594 B1 | 11/2001 | Kim et al. | |
| 6,440,935 B1 | 8/2002 | Jaynes et al. | |
| 6,642,203 B1 | 11/2003 | Destoumieux et al. | |
| 6,699,689 B1 | 3/2004 | Kim et al. | |
| 2002/0025918 A1 | 2/2002 | Jaynes | |

(Continued)

FOREIGN PATENT DOCUMENTS

EP        0 525 508 A2    2/1993

(Continued)

OTHER PUBLICATIONS

Casteels, P., "Apidaecins: antibacterial peptides from honeybees" et al., *EMBO Journal*, 8(8):2387-2391 (Aug 1989).

(Continued)

*Primary Examiner*—Chih-Min Kam
(74) *Attorney, Agent, or Firm*—TraskBritt

(57) ABSTRACT

The subject invention relates to a low cost method of producing peptides, including antimicrobial peptides (AMPs), by using microbes. The subject methods enable greatly improved yields of the peptide/AMP as compared to those heretofore known in the art. The subject methods also surprisingly enable the use of *Pseudomonas fluorescens* to produce AMPs and other peptides. There are several components of the subject invention, which can be used alone or in combination. The subject invention provides for the production of peptides/AMPs in concatemeric precursors. The subject invention also provides novel methods of assembling monomers into multimers, and of cleaving the multimers to yield active monomers. The subject invention also relates to the use of these multimers fused to carrier peptides to produce fusion proteins. Preferably, both the multimers and the fusion proteins (multimers with the carrier polypeptides) lack charge balancing. It has been surprisingly determined that it is not necessary to offset the positive charges of multiple copies of AMPs in multimeric constructs. Thus, the subject invention enables the use of a wider range of multimers and carrier peptides.

29 Claims, 4 Drawing Sheets

U.S. PATENT DOCUMENTS

| | | |
|---|---|---|
| 2002/0107174 A1 | 8/2002 | Paus et al. |
| 2003/0087823 A1 | 5/2003 | Paus et al. |

FOREIGN PATENT DOCUMENTS

| | | |
|---|---|---|
| EP | 0525508 A2 | 2/1993 |
| JP | 02-204500 | 8/1990 |
| WO | 90/12866 | 11/1990 |
| WO | 96/28559 | 3/1996 |
| WO | 97/22624 | 6/1997 |
| WO | 97/33908 | 9/1997 |
| WO | WO 97/35009 | 9/1997 |
| WO | WO 98/33908 A1 | 9/1997 |
| WO | 98/54336 | 12/1998 |
| WO | 99/05270 | 2/1999 |
| WO | 99/48912 | 9/1999 |
| WO | 99/64611 | 12/1999 |
| WO | 00/01400 | 1/2000 |
| WO | 00/34312 | 6/2000 |
| WO | WO 00/31279 A2 | 6/2000 |
| WO | WO 00/34312 A1 | 6/2000 |
| WO | WO 03/068926 | 8/2003 |

OTHER PUBLICATIONS

Casteels-Josson, K., et al., "Apidaecin multipeptide precursor structure: a putative mechanism for amplification of the insect antibacterial response," *EMBO Journal*, 12(4):1569-1578 (Apr. 1993).

Cho, J.H., et al., "Lumbricin 1, a novel proline-rich antimicrobial peptide from the earthworm: purification, cDNA cloning and molecular characterization," *Biochimica et Biophysica Acta*, 1408(1):67-76 (Oct. 22, 1998).

Cohen et al., *DNA*, 5(4):334-345 (1986).

Durll, S.R., et al., "Modeling the ion channel structure of cecropin," *Biophysical Journal*, 63(6):1623-1631 (Dec. 1992).

Gazit, E., et al., "Interaction of the mammalian antibacterial peptide cecropin P1 with phospholipid vesicles," *Biochemistry*, 34(36):11479-11488 (Sep. 12, 1995).

Hancock, R.E., et al., "Cationic bactericidal peptides," *Advances in Microbial Physiology*, 37:135-175 (1995).

Hetru, C., et al., Androctonin, a hydrophilic disulphide-bridged non-haemolytic anti-microbial peptide: a plausible mode of action, *Biochemical Journal*, 345(Pt 3):653-664 (Feb. 1, 2000).

Hultman, D., et al., "Insect immunity. Attacins, a family of antibacterial proteins from Hyalophora cecropia," *EMBO Journal*, 2(4):571-576 (1983).

Iwanaga, S., et al., "Evolution and phylogeny of defense molecules associated with innate immunity in horseshoe crab," *Frontiers in Bioscience*, 3:D973-D984 (Sep. 1, 1998).

Kim, S.C., et al., "Amplification of cloned DNA as tandem multimers using BspMI-generated asymmetric cohesive ends," *Gene*, 71(1):1-8 (Nov. 15, 1988).

Lee, J.H., et al., "Acidic peptide-mediated expression of the antimicrobial peptide buforin II as tandem repeats in *Escherichia coli*.," *Protein Expression and Purification*, 12(1):53-60 (Feb. 1998).

Lee, J.H., et al., "Multimeric expression of the antimicrobial peptide buforin II in *Escherichia coli* by fusion to a cysteine-rich acidic peptide," *J. Microbiol. Biotech.*, 9(3):303-310 (Jun. 1999).

Lee, J.H., et al., "Multimeric expression of the antimicrobial peptide buforin II in *Escherichia coli* by fusion to a cysteine-rich acidic peptide," *J. Microbiol. Biotechnol.*, 8(1):34-41 (1998).

Lee, J.H., et al., "Sequential amplification of cloned DNA as tandem multimers using class-IIS restriction enzymes," *Genetic Analysis*, 13(6):139-145 (Dec. 1996).

Leippe, M., et al., "Antimicrobial and cytolytic polypeptides of amoeboid protozoa-effector molecules of primitive phagocytes," *Developmental and Comparative Immunology*, 23(4-5):267-279 (Jun-Jul. 1999).

Mitta, G., et al., "Mussel defensins are synthesised and processed in granulocytes then released into the plasma after bacterial challenge," *Journal of Cell Science*, 112(Pt 23):4233-4242 (Dec. 1999).

Niidome, T., et al., *Peptide Science*, 36:403-406 (1999).

Norelli, J.L., et al., *Phytopathology*, 89:S56 (1999).

Padgett, T., et al., "Incorporation of food-grade antimicrobial compounds into biodegradable packaging films.," *Journal of Food Protection*, 61(10):1330-1335 (Oct. 1998).

Pardi, A., et al., "NMR studies of defensin antimicrobial peptides. 2. Three-dimensional structures of rabbit NP-2 and human HNP-1," *Biochemistry*, 31(46):11357-11364 (Nov. 24, 1992).

Rao, R., et al., "Synthesis and expression of genes encoding putative insect neuropeptide precursors in tobacco," *Gene*, 175(1-2):1-5 (Oct. 10, 1996).

Selsted, M.E., et al., "Indolicidin, a novel bactericidal tridecapeptide amide from neutrophils," *Journal of Biological Chemistry*, 267(7):4292-4295 (Mar. 5, 1992).

Sousa, L.B., et al., "The use of synthetic Cecropin (D5C) in disinfecting contact lens solutions," *CLAO Journal*, 22(2):114-117 (Apr. 1996).

Swartz, J.R., "Advances in *Escherichia coli* production of therapeutic proteins," *Current Opinion in Biotechnology*, 12(2):195-201 (Apr. 2001).

Zasloff, M., et al., "Magainins, a class of antimicrobial peptides from Xenopus skin: isolation, characterization of two active forms, and partial cDNA sequence of a precursor," *Proceedings of the National Academy of Sciences, U.S.A.*, 84(15):5449-5453 (Aug. 1987).

Zhang, L., et al., "Determinants of recombinant production of antimicrobial cationic peptides and creation of peptide variants in bacteria," *Biochemical and Biophysical Research Communications*, 247(3):674-680 (Jun. 29, 1998).

Fang et al., "The Application of Biotechnology in the Improvement of Biodefence Microorganisms," Bi-Engineering Developments, 1995, vol. 15, No. 4, pp. 42-45, Translation Attached.

Gavit et al., "Production of antifungal recombinant peptides in *Escherichia coli*," Journal of Biotechnology, vol. 79, No. 2, Apr. 28, 2000, pp. 127-136, XP000922726.

Lu et al., "Construction of pMEDm12, an expression vector for protein production in Psudomonas syringae," FEMS Microbiology Letters, vol. 210, No. 1, Apr. 11, 2002, pp. 115-121, XP002416785 ISSN: 0378-1097.

Lushbaugh et al., "Use of intravaginal microbicides to prevent acquisition of trichomonas vaginalis infection in lactobacillus-pretreated, estrogenized young mice," Am. J. Trop. Med., vol. 63, No. 5, Nov. 2000, pp. 284-289, XP002975259.

Unge et al., "Monitoring population size, activity, and distribution of gfp-luxAB-tagged Pseudomonas fluorescens SBW25 during colonization of wheat," Microbial Ecology, vol. 41, No. 4, May 2001, pp. 290-300, XP002416689 ISSN: 0095-3628.

Durell, Stewart R., et al., Modeling the Ion Channel Structure of Cecropin, Biophys. J., Dec. 1992, pp. 1623-1631, vol. 63.

Egal, Mariam, et al., Antiviral Effects of Synthetic Membrane-Active Peptides on Herpes Simplex Virus, Type 1, International Journal of Antimicrobial Agents, 1999, pp. 57-60, vol. 13, Elsevier Science B.V.

Gazit, Ehud, et al., Interaction of the Mammalian Antibacterial Peptide Cecropin P1 with Phosphilipid Vesicles, Biochemistry, 1995, pp. 11479-114, vol. 34, American Chemical Society.

Haeberli, Stefanie, et al., Characterisation of Antibacterial Activity of Peptides Isolated From the Venom of the Spider *Cupiennius Salei* (Araneae: Ctenidae), Toxicon, 2000, pp. 378-380, vol. 38.

Hancock, Robert E., et al., Cationic Peptides: a New Source of Antibiotics, TIBTECH, 1998, pp. 82-88, vol. 16.

Houghten, Richard A., et al., Mixture-Based Synthetic Combinatorial Libraries, Journal of Medicinal Chemistry, 1999, pp. 3743-3778, vol. 42., No. 19, The American Chemical Society.

Hultmark, D., et al., Insect Immunity. Attacins, a Family of Antibacterial Proteins From Hyalophora Cecropia, The EMBO Journal, 1983, pp. 571-576, vol. 2, No. 4.

Lee, Jae H., et al., Sequential Amplification of Cloned DNA as Tandem Multimers Using Class-IIS Restriction Enzymes, Genetic Analysis: Biomolecular Engineering, 1996, pp. 139-145, vol. 13, Elsevier Science.

Kim, Sun C., et al., Amplification of Cloned DNA as Tandem Multimers Using BspMI-Generated Asymmetric Cohesive Ends, Gene, 1988, pp. 1-8, vol. 71.

Sousa, M.D., L.B., et al., The Use of Synthetic Cecropin (D5C) in Disinfecting Contact Lens Solutions, The CLAO Journal, Apr. 1996, pp. 114-115, vol. 22, No. 2.

Tamamura, Hirokazu, et al., Effective Lowly Cytotoxic Analogs of an HIV-Cell Fusion Inhibitor, T22 ([Tyr 5,12, Lys 7]-Polyphemusin II), Bioorganic & Medicinal Chemistry, 1998, pp. 231-238, vol. 6, Elsevier Science.

Keller, G.H., et al., DNA Probes, 1987, pp. 169-170, Stockton Press, New York, New York.

* cited by examiner

| Ligation of termini | | Resulting Sequence: | |
|---|---|---|---|
| 3'  　　　　5' | | 5'  　　　3' | |
| C ..... GATCCG | → | CGATCCG | (desired orientation) |
| GCTAG ..... GC | | GCTAGGC | Non-palindromic sequence which encodes Asp-Pro dipeptide when inserted in pET21b vector |

Figure 3A

Ligation of identical, symmetric ends results in palindrome formation:

| C ..... GATCG | → | CGATCG | Palindromic Pvu I site (undesired) |
|---|---|---|---|
| GCTAG ..... C | | GCTAGC | |

Figure 3B

Ligation of identical, symmetric ends results in palindrome formation:

| G ..... GATCC | → | GGATCC | Palindromic BamH I site (undesired) |
|---|---|---|---|
| CCTAG ..... G | | CCTAGG | |

Figure 3C

SEQUENCE LISTING

```
<160> NUMBER OF SEQ ID NOS: 45

<210> SEQ ID NO 1
<211> LENGTH: 23
<212> TYPE: PRT
<213> ORGANISM: Artificial Sequence
<220> FEATURE:
<223> OTHER INFORMATION: Amino acid sequence for the core D2A21
      antimicrobial peptide.

<400> SEQUENCE: 1

Phe Ala Lys Lys Phe Ala Lys Lys Phe Lys Lys Phe Ala Lys Lys Phe
1               5                   10                  15

Ala Lys Phe Ala Phe Ala Phe
            20

<210> SEQ ID NO 2
<211> LENGTH: 69
<212> TYPE: DNA
<213> ORGANISM: Artificial Sequence
<220> FEATURE:
<223> OTHER INFORMATION: DNA sequence used to encode the peptide of
      SEQ ID NO:1.

<400> SEQUENCE: 2
ttcgcgaaga agtttgcgaa aaagttcaag aaatttgcca agaagtttgc caagttcgca      60
ttcgcgttc                                                              69

<210> SEQ ID NO 3
<211> LENGTH: 78
```

```
<212> TYPE: DNA
<213> ORGANISM: Artificial Sequence
<220> FEATURE:
<223> OTHER INFORMATION: DNA sequence used to encode the peptide of
      SEQ ID NO:4.

<400> SEQUENCE: 3
gatccgttcg cgaagaagtt tgcgaaaaag ttcaagaaat tgccaagaa gtttgccaag      60 ttcgcattcg cgttcggc                                                   78

<210> SEQ ID NO 4
<211> LENGTH: 26
<212> TYPE: PRT
<213> ORGANISM: Artificial Sequence
<220> FEATURE:
<223> OTHER INFORMATION: Amino acid sequence for the core D2A21
      antimicrobial peptide monomer with three additional amino acid
      residues for peptide linkage/cleavage sites for assembling into
      a multimer.

<400> SEQUENCE: 4

Asp Pro Phe Ala Lys Lys Phe Ala Lys Lys Phe Lys Lys Phe Ala Lys
1               5                   10                  15

Lys Phe Ala Lys Phe Ala Phe Ala Phe Gly
            20                  25

<210> SEQ ID NO 5
<211> LENGTH: 255
<212> TYPE: DNA
<213> ORGANISM: Artificial Sequence
<220> FEATURE:
<223> OTHER INFORMATION: DNA sequence that was used to encode the 4A
      dimer of SEQ ID NO:6 (using E. coli expression vector pET21b).

<400> SEQUENCE: 5
atggctagca tgactggtgg acagcaaatg ggtcgggatc cgttcgcgaa gaagtttgcg      60
aaaaagttca gaaattcgc gaagaagttt gccaagttcg cattcgcgtt cggggatccg     120
ttcgcgaaga gtttgcgaa aaagttcaag aaattcgcga gaagtttgc caagttcgca     180 ttcgcgttcg gggatccgaa ttcgagctcc gtcgacaagc ttgcggccgc actcgagcac     240
caccaccacc accac                                                     255

<210> SEQ ID NO 6
<211> LENGTH: 85
<212> TYPE: PRT
<213> ORGANISM: Artificial Sequence
<220> FEATURE:
<223> OTHER INFORMATION: Amino acid sequence of the 4A dimer.

<400> SEQUENCE: 6

Met Ala Ser Met Thr Gly Gly Gln Gln Met Gly Arg Asp Pro Phe Ala
1               5                   10                  15

Lys Lys Phe Ala Lys Lys Phe Lys Lys Phe Ala Lys Lys Phe Ala Lys
            20                  25                  30

Phe Ala Phe Ala Phe Gly Asp Pro Phe Ala Lys Lys Phe Ala Lys Lys
        35                  40                  45

Phe Lys Lys Phe Ala Lys Lys Phe Ala Lys Phe Ala Phe Ala Phe Gly
    50                  55                  60

Asp Pro Asn Ser Ser Ser Val Asp Lys Leu Ala Ala Ala Leu Glu His
65                  70                  75                  80

His His His His His
                85
```

-continued

```
<210> SEQ ID NO 7
<211> LENGTH: 26
<212> TYPE: PRT
<213> ORGANISM: Artificial Sequence
<220> FEATURE:
<223> OTHER INFORMATION: Amino acid sequence of the D2A21' AMP monomer.

<400> SEQUENCE: 7

Pro Phe Ala Lys Lys Phe Ala Lys Lys Phe Lys Lys Phe Ala Lys Lys
1               5                   10                  15

Phe Ala Lys Phe Ala Phe Ala Phe Gly Asp
            20                  25

<210> SEQ ID NO 8
<211> LENGTH: 6
<212> TYPE: DNA
<213> ORGANISM: Artificial Sequence
<220> FEATURE:
<223> OTHER INFORMATION: Preferred hexanucleotide sequence that encodes
      the Asp-Pro cleavable dipeptide linker.

<400> SEQUENCE: 8 gatccg                                                                    6

<210> SEQ ID NO 9
<211> LENGTH: 159
<212> TYPE: PRT
<213> ORGANISM: Artificial Sequence
<220> FEATURE:
<223> OTHER INFORMATION: Amino acid sequence of the AB4 trimer.

<400> SEQUENCE: 9

Met Ala Ser Met Thr Gly Gly Gln Gln Met Gly Arg Asp Pro Phe Ala
1               5                   10                  15

Lys Lys Phe Ala Lys Lys Phe Lys Lys Phe Ala Lys Lys Phe Ala Lys
                20                  25                  30

Phe Ala Phe Ala Phe Gly Asp Pro Phe Ala Lys Lys Phe Ala Lys Lys
            35                  40                  45

Phe Lys Lys Phe Ala Lys Lys Phe Ala Lys Phe Ala Phe Ala Phe Gly
        50                  55                  60

Asp Pro Phe Ala Lys Lys Phe Ala Lys Lys Phe Lys Lys Phe Ala Lys
65                  70                  75                  80

Lys Phe Ala Lys Phe Ala Phe Ala Phe Gly Asp Pro Ser Arg Arg Ser
                85                  90                  95

Leu Arg Lys Ser Ser Arg Asn Leu Pro Arg Ser Leu Pro Ser Ser His
            100                 105                 110

Ser Arg Ser Val Ile Arg Ile Arg Ala Pro Ser Thr Ser Leu Arg Pro
        115                 120                 125

His Ser Ser Thr Thr Thr Thr Thr Glu Ile Arg Leu Leu Thr Lys
    130                 135                 140

Pro Glu Arg Lys Leu Ser Trp Leu Leu Pro Pro Leu Ser Asn Asn
145                 150                 155

<210> SEQ ID NO 10
<211> LENGTH: 480
<212> TYPE: DNA
<213> ORGANISM: Artificial Sequence
<220> FEATURE:
<223> OTHER INFORMATION: DNA sequence that was used to encode the AB4
      trimer of SEQ ID NO:9 (in E. coli expression vector pET21b).
```

-continued

```
<400> SEQUENCE: 10
atggctagca tgactggtgg acagcaaatg ggtcgggatc cgttcgcgaa gaagtttgcg        60
aaaaagttca gaaatttgc caagaagttt gccaagttcg cattcgcgtt cggcgatccg       120
ttcgcgaaga gtttgcgaa aaagttcaag aaatttgcca gaagtttgc caagttcgca       180 ttcgcgttcg gcgatccgtt cgcgaagaag tttgcgaaaa agttcaagaa atttgccaag      240
aagtttgcca gttcgcatt cgcgttcggc gatccttcgc gaagaagttt gcgaaaaagt      300
tcaagaaatt tgccaagaag tttgccaagt cgcattcgc gttcggtgat ccgaattcga      360
gctccgtcga caagcttgcg gccgcactcg agcaccacca ccaccaccac tgagatccgg      420
ctgctaacaa agcccgaaag gaagctgagt tggctgctgc caccgctgag caataactag      480
```

<210> SEQ ID NO 11
<211> LENGTH: 159
<212> TYPE: PRT
<213> ORGANISM: Artificial Sequence
<220> FEATURE:
<223> OTHER INFORMATION: Amino acid sequence of the TF3 trimer.

<400> SEQUENCE: 11

```
Met Ala Ser Met Thr Gly Gly Gln Gln Met Gly Arg Asp Pro Phe Ala
 1               5                  10                  15

Lys Lys Phe Ala Lys Lys Phe Lys Lys Phe Ala Lys Lys Phe Ala Lys
                20                  25                  30

Phe Ala Phe Ala Phe Gly Asp Pro Phe Ala Lys Lys Phe Ala Lys Lys
            35                  40                  45

Phe Lys Lys Phe Ala Lys Lys Phe Ala Lys Phe Ala Phe Ala Phe Gly
        50                  55                  60

Asp Pro Phe Ala Lys Lys Phe Ala Lys Lys Phe Lys Lys Phe Ala Lys
 65                  70                  75                  80

Lys Phe Ala Lys Phe Ala Phe Ala Phe Gly Asp Pro Ser Arg Arg Ser
                85                  90                  95

Leu Arg Lys Ser Ser Arg Asn Leu Pro Arg Ser Leu Pro Ser Ser His
               100                 105                 110

Ser Arg Ser Val Ile Arg Ile Arg Ala Pro Ser Thr Ser Leu Arg Pro
           115                 120                 125

His Ser Ser Thr Thr Thr Thr Thr Glu Ile Arg Leu Leu Thr Lys
       130                 135                 140

Pro Glu Arg Lys Leu Ser Trp Leu Leu Pro Leu Ser Asn Asn
145                 150                 155
```

<210> SEQ ID NO 12
<211> LENGTH: 481
<212> TYPE: DNA
<213> ORGANISM: Artificial Sequence
<220> FEATURE:
<223> OTHER INFORMATION: DNA sequence used to encode the TF3 trimer of
      SEQ ID NO:11 (in P. fluorescens expression vector pMYC1803).

<400> SEQUENCE: 12

```
atggctagca tgactggtgg acagcaaatg ggtcgggatc cgttcgcgaa gaagtttgcg        60
aaaaagttca gaaatttgc caagaagttt gccaagttcg cattcgcgtt cggcgatccg       120
ttcgcgaaga gtttgcgaa aaagttcaag aaatttgcca gaagtttgc caagttcgca       180 ttcgcgttcg gcgatccgtt cgcgaagaag tttgcgaaaa agttcaagaa atttgccaag      240
aagtttgcca gttcgcatt cgcgttcggc gatccttcgc gaagaagttt gcgaaaaagt      300
```

```
tcaagaaatt tgccaagaag tttgccaagt tcgcattcgc gttcggtgat ccgaattcga    360
gctccgtcga caagcttgcg gccgcactcg agcaccacca ccaccaccac tgagatccgg    420
ctgctaacaa agcccgaaag gaagctgagt tggctgctgc caccgctgag caataactaa    480
t                                                                   481
```

<210> SEQ ID NO 13
<211> LENGTH: 17
<212> TYPE: PRT
<213> ORGANISM: Artificial Sequence
<220> FEATURE:
<223> OTHER INFORMATION: Amino acid sequence of the D4E1 AMP.

<400> SEQUENCE: 13

```
Phe Lys Leu Arg Ala Lys Ile Lys Val Arg Leu Arg Ala Lys Ile Lys
 1               5                  10                  15

Leu
```

<210> SEQ ID NO 14
<211> LENGTH: 99
<212> TYPE: PRT
<213> ORGANISM: Artificial Sequence
<220> FEATURE:
<223> OTHER INFORMATION: Amino acid sequence of a D4E1 trimer.

<400> SEQUENCE: 14

```
Met Ala Ser Met Thr Gly Gly Gln Gln Met Gly Arg Asp Pro Phe Lys
 1               5                  10                  15

Leu Arg Ala Lys Ile Lys Val Arg Leu Arg Ala Lys Ile Lys Leu Gly
                20                  25                  30

Asp Pro Asp Pro Phe Lys Leu Arg Ala Lys Ile Lys Val Arg Leu Arg
            35                  40                  45

Ala Lys Ile Lys Leu Gly Asp Pro Asp Pro Phe Lys Leu Arg Ala Lys
        50                  55                  60

Ile Lys Val Arg Leu Arg Ala Lys Ile Lys Leu Gly Asp Pro Asp Pro
65                  70                  75                  80

Asn Ser Ser Ser Val Asp Lys Leu Ala Ala Ala Leu Glu His His His
                85                  90                  95

His His His
```

<210> SEQ ID NO 15
<211> LENGTH: 300
<212> TYPE: DNA
<213> ORGANISM: Artificial Sequence
<220> FEATURE:
<223> OTHER INFORMATION: DNA sequence used to encode the D4E1 trimer of
      SEQ ID NO:14 (in P. fluorescens expression vector pMYC1803 and E.
      coli expression vector pET24b).

<400> SEQUENCE: 15

```
atggctagca tgactggtgg acagcaaatg ggtcgggatc cgttcaaact gcgtgctaaa    60
atcaaagttc gtctgcgtgc taaaatcaaa ctgggtgacc ctgatccgtt caaactgcgt    120
gctaaaatca agttcgtctc gcgtgctaaa atcaaactgg gtgaccctga tccgttcaaa    180
ctgcgtgcta aaatcaaagt tcgtctgcgt gctaaaatca aactgggtga ccctgatccg    240
aattcgagct ccgtcgacaa gcttgcggcc gcactcgagc accaccacca ccaccactga    300
```

<210> SEQ ID NO 16
<211> LENGTH: 121
<212> TYPE: PRT

<213> ORGANISM: Artificial Sequence
<220> FEATURE:
<223> OTHER INFORMATION: Amino acid sequence of the D4E1 tetramer.

<400> SEQUENCE: 16

```
Met Ala Ser Thr Thr Gly Gly Gln Gln Met Gly Arg Asp Pro Phe Lys
1               5                   10                  15

Leu Arg Ala Lys Ile Lys Val Arg Leu Arg Ala Lys Ile Lys Leu Gly
            20                  25                  30

Asp Pro Asp Pro Phe Lys Leu Arg Ala Lys Ile Lys Val Arg Leu Arg
        35                  40                  45

Ala Lys Ile Lys Leu Gly Asp Pro Asp Pro Phe Lys Leu Arg Val Lys
    50                  55                  60

Ile Lys Val Arg Leu Arg Ala Lys Ile Lys Leu Gly Asp Pro Asp Pro
65                  70                  75                  80

Phe Lys Leu Arg Ala Lys Ile Lys Val Arg Leu Arg Ala Lys Ile Lys
                85                  90                  95

Leu Gly Asp Pro Asp Pro Asn Ser Ser Ser Val Asp Lys Leu Ala Ala
            100                 105                 110

Ala Leu Glu His His His His His His
        115                 120
```

<210> SEQ ID NO 17
<211> LENGTH: 366
<212> TYPE: DNA
<213> ORGANISM: Artificial Sequence
<220> FEATURE:
<223> OTHER INFORMATION: DNA sequence used to encode the D4E1 tetramer
      of SEQ ID NO:16 (in P. fluorescens expression vector pMYC1803).

<400> SEQUENCE: 17

```
atggctagca cgactggtgg acagcaaatg ggtcgggatc cgttcaaact gcgtgctaaa    60
atcaaagttc gtctgcgtgc taaaatcaaa ctgggtgacc ctgatccgtt caaactgcgt   120
gctaaaatca agttcgtct gcgtgctaaa atcaaactgg gtgaccctga tccgttcaaa   180
ctgcgtgtta aaatcaaagt tcgtctgcgt gctaaaatca aactgggtga ccctgatccg   240
ttcaaactgc gtgctaaaat caaagttcgt ctgcgtgcta aaatcaaact gggtgaccct   300
gatccgaatt cgagctccgt cgacaagctt gcggccgcac tcgagcacca ccaccaccac   360
cactga                                                             366
```

<210> SEQ ID NO 18
<211> LENGTH: 143
<212> TYPE: PRT
<213> ORGANISM: Artificial Sequence
<220> FEATURE:
<223> OTHER INFORMATION: Amino acid sequence of the D4E1 pentamer.

<400> SEQUENCE: 18

```
Met Ala Ser Met Thr Gly Gly Gln Gln Met Gly Arg Asp Pro Phe Lys
1               5                   10                  15

Leu Arg Ala Lys Ile Lys Val Arg Leu Arg Ala Lys Ile Lys Leu Gly
            20                  25                  30

Asp Pro Asp Pro Phe Lys Leu Arg Ala Lys Ile Lys Val Arg Leu Arg
        35                  40                  45

Ala Lys Ile Lys Leu Gly Asp Pro Asp Pro Phe Lys Leu Arg Ala Lys
    50                  55                  60

Ile Lys Val Arg Leu Arg Ala Lys Ile Lys Leu Gly Asp Pro Asp Pro
65                  70                  75                  80
```

```
Phe Lys Leu Arg Ala Lys Ile Lys Val Arg Leu Arg Ala Lys Ile Lys
                85                  90                  95

Leu Gly Asp Pro Asp Pro Phe Lys Leu Arg Ala Lys Ile Lys Val Arg
            100                 105                 110

Leu Arg Ala Lys Ile Lys Leu Gly Asp Pro Asp Pro Asn Ser Ser Ser
        115                 120                 125

Val Asp Lys Leu Ala Ala Ala Leu Glu His His His His His His
    130                 135                 140
```

<210> SEQ ID NO 19
<211> LENGTH: 432
<212> TYPE: DNA
<213> ORGANISM: Artificial Sequence
<220> FEATURE:
<223> OTHER INFORMATION: DNA sequence used to encode the D4E1 pentamer
      of SEQ ID NO:18 (in P. fluorescens expression vector pMYC1803 and
      E. coli expression vector pET24b).

<400> SEQUENCE: 19

```
atggctagca tgactggtgg acagcaaatg ggtcgggatc cgttcaaact gcgtgctaaa    60
atcaaagttc gtctgcgtgc taaaatcaaa ctgggtgacc ctgatccgtt caaactgcgt   120
gctaaaatca agttcgtctg cgtgctaaa atcaaactgg gtgaccctga tccgttcaaa   180
ctgcgtgcta aaatcaaagt tcgtctgcgt gctaaaatca aactgggtga ccctgatccg   240
ttcaaactgc gtgctaaaat caaagttcgt ctgcgtgcta aaatcaaact gggtgaccct   300
gatccgttca aactgcgtgc taaaatcaaa gttcgtctgc gtgctaaaat caaactgggt   360
gaccctgatc cgaattcgag ctccgtcgac aagcttgcgg ccgcactcga gcaccaccac   420
caccaccact ga                                                      432
```

<210> SEQ ID NO 20
<211> LENGTH: 162
<212> TYPE: PRT
<213> ORGANISM: Artificial Sequence
<220> FEATURE:
<223> OTHER INFORMATION: Amino acid sequence of the dihydrofolate
      reductase (DHFR) protein.

<400> SEQUENCE: 20

```
Met Val Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140
```

```
Ala Gln Asn Ser His Ser Tyr Glu Phe Glu Ile Leu Glu Arg Arg Gly
145                 150                 155                 160

Ser Ala

<210> SEQ ID NO 21
<211> LENGTH: 486
<212> TYPE: DNA
<213> ORGANISM: Artificial Sequence
<220> FEATURE:
<223> OTHER INFORMATION: DNA sequence of the DHFR gene encoding the
      dehalogenase protein of SEQ ID NO:20 (in P. fluorescens expression
      vector pMYC1803).

<400> SEQUENCE: 21
atggtcagtc tgattgcggc gttagcggta gatcgcgtta tcggcatgga aaacgccatg      60
ccgtggaacc tgcctgccga tctcgcctgg tttaaacgca acaccttaaa taaacccgtg     120
attatgggcc gccataccty ggaatcaatc ggtcgtccgt tgccaggacg caaaaatatt     180
atcctcagca gtcaaccggg tacggacgat cgcgtaacgt gggtgaagtc ggtggatgaa     240
gccatcgcgg cgtgtggtga cgtaccagaa atcatggtga ttggcggcgg tcgcgtttat     300
gaacagttct tgccaaaagc gcaaaaactg tatctgacgc atatcgacgc agaagtggaa     360
ggcgacaccc atttcccgga ttacgagccg gatgactggg aatcggtatt cagcgaattc     420
cacgatgctg atgcgcagaa ctctcacagc tatgagtttg agattctgga gcggcgggga     480
tccgcc                                                                486

<210> SEQ ID NO 22
<211> LENGTH: 321
<212> TYPE: PRT
<213> ORGANISM: Artificial Sequence
<220> FEATURE:
<223> OTHER INFORMATION: Amino acid sequence of the DHFR/TF3 trimer
      fusion.

<400> SEQUENCE: 22

Met Val Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Glu Phe Glu Ile Leu Glu Arg Arg Gly
145                 150                 155                 160

Ser Ala Met Ala Ser Met Thr Gly Gly Gln Gln Met Gly Arg Asp Pro
                165                 170                 175
```

```
Phe Ala Lys Lys Phe Ala Lys Lys Phe Lys Lys Phe Ala Lys Lys Phe
                180                 185                 190
Ala Lys Phe Ala Phe Ala Phe Gly Asp Pro Phe Ala Lys Lys Phe Ala
            195                 200                 205
Lys Lys Phe Lys Lys Phe Ala Lys Lys Phe Ala Lys Phe Ala Phe Ala
        210                 215                 220
Phe Gly Asp Pro Phe Ala Lys Lys Phe Ala Lys Lys Phe Lys Lys Phe
225                 230                 235                 240
Ala Lys Lys Phe Ala Lys Phe Ala Phe Ala Phe Gly Asp Pro Ser Arg
            245                 250                 255
Arg Ser Leu Arg Lys Ser Ser Arg Asn Leu Pro Arg Ser Leu Pro Ser
            260                 265                 270
Ser His Ser Arg Ser Val Ile Arg Ile Arg Ala Pro Ser Thr Ser Leu
        275                 280                 285
Arg Pro His Ser Ser Thr Thr Thr Thr Thr Thr Glu Ile Arg Leu Leu
        290                 295                 300
Thr Lys Pro Glu Arg Lys Leu Ser Trp Leu Leu Pro Pro Leu Ser Asn
305                 310                 315                 320
Asn

<210> SEQ ID NO 23
<211> LENGTH: 967
<212> TYPE: DNA
<213> ORGANISM: Artificial Sequence
<220> FEATURE:
<223> OTHER INFORMATION: DNA sequence used to encode the fusion of
      SEQ ID NO:22 (in P. fluorescens expression vector pMYC1803).

<400> SEQUENCE: 23
atggtcagtc tgattgcggc gttagcggta gatcgcgtta tcggcatgga aaacgccatg      60
ccgtggaacc tgcctgccga tctcgcctgg tttaaacgca acaccttaaa taaacccgtg     120
attatgggcc gccataccig ggaatcaatc ggtcgtccgt tgccaggacg caaaatatt      180 atcctcagca gtcaaccggg tacgacgat cgcgtaacgt gggtgaagtc ggtggatgaa      240
gccatcgcgg cgtgtggtga cgtaccagaa atcatggtga ttggcggcgg tcgcgtttat     300
gaacagttct tgccaaaagc gcaaaaactg tatctgacgc atatcgacgc agaagtggaa     360
ggcgacaccc atttcccgga ttacgagccg gatgactggg aatcggtatt cagcgaattc     420
cacgatgctg atgcgcagaa ctctcacagc tatgagtttg agattctgga gcggcgggga     480
tccgccatgg ctagcatgac tggtggacag caaatgggtc gggatccgtt cgcgaagaag     540
tttgcgaaaa agttcaagaa atttgccaag aagtttgcca agttcgcatt cgcgttcggc     600
gatccgttcg cgaagaagtt tgcgaaaaag ttcaagaaat tgccaagaa gtttgccaag      660 ttcgcattcg cgttcggcga tccgttcgcg aagaagtttg cgaaaaagtt caagaaattt     720
gccaagaagt ttgccaagtt cgcattcgcg ttcggcgatc cttcgcgaag aagtttgcga     780
aaaagttcaa gaaatttgcc aagaagtttg ccaagttcgc attcgcgttc ggtgatccga     840
attcgagctc cgtcgacaag cttgcggccg cactcgagca ccaccaccac caccactgag     900
atccggctgc taacaaagcc cgaaaggaag ctgagttggc tgctgccacc gctgagcaat     960
aactaat                                                              967

<210> SEQ ID NO 24
<211> LENGTH: 261
<212> TYPE: PRT
<213> ORGANISM: Artificial Sequence
```

<220> FEATURE:
<223> OTHER INFORMATION: Amino acid sequence of the DHFR/D4E1 trimer fusion.

<400> SEQUENCE: 24

```
Met Val Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Glu Phe Glu Ile Leu Glu Arg Arg Gly
145                 150                 155                 160

Ser Ala Met Ala Ser Met Thr Gly Gly Gln Gln Met Gly Arg Asp Pro
                165                 170                 175

Phe Lys Leu Arg Ala Lys Ile Lys Val Arg Leu Arg Ala Lys Ile Lys
            180                 185                 190

Leu Gly Asp Pro Asp Pro Phe Lys Leu Arg Ala Lys Ile Lys Val Arg
        195                 200                 205

Leu Arg Ala Lys Ile Lys Leu Gly Asp Pro Asp Pro Phe Lys Leu Arg
    210                 215                 220

Ala Lys Ile Lys Val Arg Leu Arg Ala Lys Ile Lys Leu Gly Asp Pro
225                 230                 235                 240

Asp Pro Asn Ser Ser Ser Val Asp Lys Leu Ala Ala Ala Leu Glu His
                245                 250                 255

His His His His
        260
```

<210> SEQ ID NO 25
<211> LENGTH: 786
<212> TYPE: DNA
<213> ORGANISM: Artificial Sequence
<220> FEATURE:
<223> OTHER INFORMATION: DNA sequence used to encode the fusion of SEQ ID NO:24 (in P. fluorescens expression vector pMYC1803).

<400> SEQUENCE: 25

```
atggtcagtc tgattgcggc gttagcggta gatcgcgtta tcggcatgga aaacgccatg      60
ccgtggaacc tgcctgccga tctcgcctgg tttaaacgca acaccttaaa taaaccgtg     120 attatgggcc gccataccctg ggaatcaatc ggtcgtccgt tgccaggacg caaaaatatt    180
atcctcagca gtcaaccggg tacggacgat cgcgtaacgt gggtgaagtc ggtggatgaa    240
gccatcgcgg cgtgtggtga cgtaccagaa atcatggtga ttggcggcgg tcgcgtttat    300
gaacagttct tgccaaaagc gcaaaaactg tatctgacgc atatcgacgc agaagtggaa    360
```

-continued

```
ggcgacaccc atttcccgga ttacgagccg gatgactggg aatcggtatt cagcgaattc    420
cacgatgctg atgcgcagaa ctctcacagc tatgagtttg agattctgga gcggcgggga    480
tccgccatgg ctagcatgac tggtggacag caaatgggtc gggatccgtt caaactgcgt    540
gctaaaatca agttcgtctc gcgtgctaaa atcaaactgg gtgaccctga tccgttcaaa    600
ctgcgtgcta aaatcaaagt tcgtctgcgt gctaaaatca aactgggtga ccctgatccg    660
ttcaaactgc gtgctaaaat caaagttcgt ctgcgtgcta aaatcaaact gggtgaccct    720
gatccgaatt cgagctccgt cgacaagctt gcggccgcac tcgagcacca ccaccaccac    780
cactga                                                               786
```

<210> SEQ ID NO 26
<211> LENGTH: 283
<212> TYPE: PRT
<213> ORGANISM: Artificial Sequence
<220> FEATURE:
<223> OTHER INFORMATION: Amino acid sequence of the DHFR/D4E1 tetramer fusion.

<400> SEQUENCE: 26

```
Met Val Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Glu Phe Glu Ile Leu Glu Arg Arg Gly
145                 150                 155                 160

Ser Ala Met Ala Ser Thr Thr Gly Gly Gln Gln Met Gly Arg Asp Pro
                165                 170                 175

Phe Lys Leu Arg Ala Lys Ile Lys Val Arg Leu Arg Ala Lys Ile Lys
            180                 185                 190

Leu Gly Asp Pro Asp Pro Phe Lys Leu Arg Ala Lys Ile Lys Val Arg
        195                 200                 205

Leu Arg Ala Lys Ile Lys Leu Gly Asp Pro Asp Pro Phe Lys Leu Arg
    210                 215                 220

Val Lys Ile Lys Val Arg Leu Arg Ala Lys Ile Lys Leu Gly Asp Pro
225                 230                 235                 240

Asp Pro Phe Lys Leu Arg Ala Lys Ile Lys Val Arg Leu Arg Ala Lys
                245                 250                 255

Ile Lys Leu Gly Asp Pro Asp Pro Asn Ser Ser Ser Val Asp Lys Leu
            260                 265                 270
```

-continued

Ala Ala Ala Leu Glu His His His His His His
        275                 280

<210> SEQ ID NO 27
<211> LENGTH: 852
<212> TYPE: DNA
<213> ORGANISM: Artificial Sequence
<220> FEATURE:
<223> OTHER INFORMATION: DNA sequence used to encode the fusion of
      SEQ ID NO:26 (in P. fluorescens expression vector pMYC1803).

<400> SEQUENCE: 27

```
atggtcagtc tgattgcggc gttagcggta gatcgcgtta tcggcatgga aaacgccatg      60
ccgtggaacc tgcctgccga tctcgcctgg tttaaacgca acaccttaaa taaacccgtg     120
attatgggcc gccatacctg ggaatcaatc ggtcgtccgt tgccaggacg caaaaatatt     180
atcctcagca gtcaaccggg tacggacgat cgcgtaacgt gggtgaagtc ggtggatgaa     240
gccatcgcgg cgtgtggtga cgtaccagaa atcatggtga ttggcggcgg tcgcgtttat     300
gaacagttct tgccaaaagc gcaaaaactg tatctgacgc atatcgacgc agaagtggaa     360
ggcgacaccc atttcccgga ttacgagccg atgactggg aatcggtatt cagcgaattc     420
cacgatgctg atgcgcagaa ctctcacagc tatgagtttg agattctgga gcggcgggga     480
tccgccatgg ctagcacgac tggtggacag caaatgggtc gggatccgtt caaactgcgt     540
gctaaaatca agttcgtct cgtgctaaa atcaaactgg gtgaccctga tccgttcaaa      600
ctgcgtgcta aaatcaaagt tcgtctgcgt gctaaaatca aactgggtga ccctgatccg     660
ttcaaactgc gtgttaaaat caaagttcgt ctgcgtgcta aaatcaaact gggtgacccct    720
gatccgttca actgcgtgc taaaatcaaa gttcgtctgc gtgctaaaat caaactgggt     780
gaccctgatc cgaattcgag ctccgtcgac aagcttgcgg ccgcactcga gcaccaccac     840
caccaccact ga                                                         852
```

<210> SEQ ID NO 28
<211> LENGTH: 305
<212> TYPE: PRT
<213> ORGANISM: Artificial Sequence
<220> FEATURE:
<223> OTHER INFORMATION: Amino acid sequence of the DHFR/D4E1 pentamer
      fusion.

<400> SEQUENCE: 28

Met Val Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

```
Glu Pro Asp Asp Trp Glu Ser Val Phe Ser Glu Phe His Asp Ala Asp
    130                 135                 140

Ala Gln Asn Ser His Ser Tyr Glu Phe Glu Ile Leu Glu Arg Arg Gly
145                 150                 155                 160

Ser Ala Met Ala Ser Met Thr Gly Gly Gln Gln Met Gly Arg Asp Pro
                165                 170                 175

Phe Lys Leu Arg Ala Lys Ile Lys Val Arg Leu Arg Ala Lys Ile Lys
            180                 185                 190

Leu Gly Asp Pro Asp Pro Phe Lys Leu Arg Ala Lys Ile Lys Val Arg
        195                 200                 205

Leu Arg Ala Lys Ile Lys Leu Gly Asp Pro Asp Pro Phe Lys Leu Arg
    210                 215                 220

Ala Lys Ile Lys Val Arg Leu Arg Ala Lys Ile Lys Leu Gly Asp Pro
225                 230                 235                 240

Asp Pro Phe Lys Leu Arg Ala Lys Ile Lys Val Arg Leu Arg Ala Lys
                245                 250                 255

Ile Lys Leu Gly Asp Pro Asp Pro Phe Lys Leu Arg Ala Lys Ile Lys
            260                 265                 270

Val Arg Leu Arg Ala Lys Ile Lys Leu Gly Asp Pro Asp Pro Asn Ser
        275                 280                 285

Ser Ser Val Asp Lys Leu Ala Ala Ala Leu Glu His His His His
    290                 295                 300

His
305

<210> SEQ ID NO 29
<211> LENGTH: 918
<212> TYPE: DNA
<213> ORGANISM: Artificial Sequence
<220> FEATURE:
<223> OTHER INFORMATION: DNA sequence used to encode the fusion of
      SEQ ID NO:28 (in P. fluorescens expression vector pMYC1803).

<400> SEQUENCE: 29
atggtcagtc tgattgcggc gttagcggta gatcgcgtta tcggcatgga aaacgccatg      60
ccgtggaacc tgcctgccga tctcgcctgg tttaaacgca acaccttaaa taaacccgtg     120
attatgggcc gccatacctg gaatcaatc ggtcgtccgt tgccaggacg caaaatatt      180 atcctcagca gtcaaccggg tacggacgat cgcgtaacgt gggtgaagtc ggtggatgaa     240
gccatcgcgg cgtgtggtga cgtaccagaa atcatggtga ttggcggcgg tcgcgtttat     300
gaacagttct tgccaaaagc gcaaaaactg tatctgacgc atatcgacgc agaagtggaa     360
ggcgacaccc atttcccgga ttacgagccg atgactggg atcggtatt cagcgaattc      420 cacgatgctg atgcgcagaa ctctcacagc tatgagtttg agattctgga gcggcgggga     480
tccgccatgg ctagcatgac tggtggacag caaatgggtc gggatccgtt caaactgcgt     540
gctaaaatca agttcgtctc gtgctaaa atcaaactgg gtgaccctga tccgttcaaa     600
ctgcgtgcta aaatcaaagt tcgtctgcgt gctaaaatca aactgggtga ccctgatccg     660
ttcaaactgc gtgctaaaat caagttcgt ctgcgtgcta aaatcaaact gggtgaccct     720
gatccgttca aactgcgtgc taaaatcaaa gttcgtctgc gtgctaaaat caaactgggt     780
gaccctgatc cgttcaaact gcgtgctaaa atcaaagttc gtctgcgtgc taaaatcaaa     840
ctgggtgacc tgatccgaa ttcgagctcc gtcgacaagc ttgcggccgc actcgagcac     900
caccaccacc accactga                                                   918
```

<210> SEQ ID NO 30
<211> LENGTH: 293
<212> TYPE: PRT
<213> ORGANISM: Rhodococcus rhodochrous TDTM003
<220> FEATURE:
<223> OTHER INFORMATION: Amino acid sequence of the full-length dehalogenase protein.

<400> SEQUENCE: 30

```
Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Ser His Arg Cys Ile Ala Pro
    50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Val Leu Pro Lys Cys
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Ile Pro Ile Ala Gly Glu Pro Ala Asn Ile Val Ala Leu Val Glu Ala
    210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu His
            260                 265                 270

Tyr Leu Gln Glu Asp Asn Pro Asp Leu Ile Gly Ser Glu Ile Ala Arg
        275                 280                 285

Trp Leu Pro Ala Leu
    290
```

<210> SEQ ID NO 31
<211> LENGTH: 879
<212> TYPE: DNA
<213> ORGANISM: Rhodococcus rhodochrous TDTM003
<220> FEATURE:
<223> OTHER INFORMATION: DNA sequence used to encode the dehalogenase protein of SEQ ID NO:30.

<400> SEQUENCE: 31

```
atgtcagaaa tcggtacagg cttcccttc gaccccatt atgtggaagt cctgggcgag    60
cgtatgcact acgtcgatgt tggaccgcgg gatggcacgc ctgtgctgtt cctgcacggt   120
aacccgacct cgtcctacct gtggcgcaac atcatcccgc atgtagcacc gagtcatcgg   180
tgcattgctc cagacctgat cgggatggga aaatcggaca accagacct cgattatttc    240 ttcgacgacc acgtccgcta cctcgatgcc ttcatcgaag ccttgggttt ggaagaggtc   300
gtcctggtca tccacgactg gggctcagct ctcggattcc actgggccaa gcgcaatccg   360
gaacgggtca aggtattgc atgtatggaa ttcatccggc ctatcccgac gtgggacgaa    420
tggccggaat cgcccgtga accttccag gccttccgga ccgccgacgt cggccgagag    480
ttgatcatcg atcagaacgc tttcatcgag ggtgtgctcc cgaaatgcgt cgtccgtccg   540
cttacggagt cgagatgga ccactatcgc gagcccttcc tcaagcctgt tgaccgagag    600
ccactgtggc gattccccaa cgagatcccc atcgccggtg agcccgcgaa catcgtcgcg   660
ctcgtcgagg catacatgaa ctggctgcac cagtcacctg tcccgaagtt gttgttctgg   720
ggcacacccg gcgtactgat cccccggcc gaagccgcga cttgccga aagcctcccc      780 aactgcaaga cagtggacat cggcccggga ttgcactacc tccaggaaga caacccggac   840
cttatcggca gtgagatcgc gcgctggctc cccgcactc                           879
```

<210> SEQ ID NO 32
<211> LENGTH: 446
<212> TYPE: PRT
<213> ORGANISM: Artificial Sequence
<220> FEATURE:
<223> OTHER INFORMATION: Amino acid sequence of the "3I" fusion
      (dehalogenase/D2A21' trimer).

<400> SEQUENCE: 32

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Ser His Arg Cys Ile Ala Pro
        50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Val Leu Pro Lys Cys
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

```
Ile Pro Ile Ala Gly Glu Pro Ala Asn Ile Val Ala Leu Val Glu Ala
    210                 215                 220
Tyr Met Asn Trp Leu His Gln Ser Pro Val Pro Lys Leu Leu Phe Trp
225                 230                 235                 240
Gly Thr Pro Gly Val Leu Ile Pro Pro Ala Glu Ala Ala Arg Leu Ala
                245                 250                 255
Glu Ser Leu Pro Asn Cys Lys Thr Val Asp Ile Gly Pro Gly Leu His
                260                 265                 270
Tyr Leu Gln Glu Asp Asn Pro Asp Leu Ile Gly Ser Glu Ile Ala Arg
                275                 280                 285
Trp Leu Pro Ala Leu Gly Gln Gln Met Gly Arg Asp Pro Phe Ala Lys
    290                 295                 300
Lys Phe Ala Lys Lys Phe Lys Lys Phe Ala Lys Lys Phe Ala Lys Phe
305                 310                 315                 320
Ala Phe Ala Phe Gly Asp Pro Phe Ala Lys Lys Phe Ala Lys Lys Phe
                325                 330                 335
Lys Lys Phe Ala Lys Lys Phe Ala Lys Phe Ala Phe Ala Phe Gly Asp
                340                 345                 350
Pro Phe Ala Lys Lys Phe Ala Lys Lys Phe Lys Lys Phe Ala Lys Lys
                355                 360                 365
Phe Ala Lys Phe Ala Phe Ala Phe Gly Asp Pro Ser Arg Arg Ser Leu
    370                 375                 380
Arg Lys Ser Ser Arg Asn Leu Pro Arg Ser Leu Pro Ser Ser His Ser
385                 390                 395                 400
Arg Ser Val Ile Arg Ile Arg Ala Pro Ser Thr Ser Leu Arg Pro His
                405                 410                 415
Ser Ser Thr Thr Thr Thr Thr Glu Ile Arg Leu Leu Thr Lys Pro
                420                 425                 430
Glu Arg Lys Leu Ser Trp Leu Leu Pro Pro Leu Ser Asn Asn
    435                 440                 445

<210> SEQ ID NO 33
<211> LENGTH: 1341
<212> TYPE: DNA
<213> ORGANISM: Artificial Sequence
<220> FEATURE:
<223> OTHER INFORMATION: DNA sequence used to encode the "3I" fusion of
      SEQ ID NO:32 (in P. fluorescens expression vector pMYC1803 and E.
      coli expression vector pET21b).

<400> SEQUENCE: 33
atgtcagaaa tcggtacagg cttccccttc gaccccatt atgtggaagt cctgggcgag      60
cgtatgcact acgtcgatgt tggaccgcgg gatggcacgc ctgtgctgtt cctgcacggt    120
aacccgacct cgtcctacct gtggcgcaac atcatcccgc atgtagcacc gagtcatcgg    180
tgcattgctc cagacctgat cgggatggga aaatcggaca accagacct cgattatttc     240 ttcgacgacc acgtccgcta cctcgatgcc ttcatcgaag ccttgggttt ggaagaggtc    300
gtcctggtca tccacgactg gggctcagct ctcggattcc actgggccaa gcgcaatccg    360
gaacgggtca aggtattgc atgtatggaa ttcatccggc ctatcccgac gtgggacgaa    420
tggccggaat cgcccgtga ccttccag gccttccga ccgccgacgt cggccgagag        480
ttgatcatcg atcagaacgc tttcatcgag ggtgtgctcc cgaaatgcgt cgtccgtccg    540 cttacgagg tcgagatgga ccactatcgc gagcccttcc tcaagcctgt tgaccgagag     600
ccactgtggc gattccccaa cgagatcccc atcgccggtg agcccgcgaa catcgtcgcg    660
```

-continued

```
ctcgtcgagg catacatgaa ctggctgcac cagtcacctg tcccgaagtt gttgttctgg    720
ggcacacccg gcgtactgat ccccccggcc gaagccgcga gacttgccga aagcctcccc    780
aactgcaaga cagtggacat cggcccggga ttgcactacc tccaggaaga caacccggac    840
cttatcggca gtgagatcgc gcgctggctc cccgcactcg gacagcaaat gggtcgggat    900
ccgttcgcga agaagtttgc gaaaaagttc aagaaatttg ccaagaagtt tgccaagttc    960
gcattcgcgt tcggcgatcc gttcgcgaag aagtttgcga aaagttcaa gaaatttgcc   1020 aagaagtttg ccaagttcgc attcgcgttc ggcgatccgt tcgcgaagaa gtttgcgaaa   1080
aagttcaaga aatttgccaa gaagtttgcc aagttcgcat tcgcgttcgg cgatccttcg   1140
cgaagaagtt tgcgaaaaag ttcaagaaat tgccaagaa gtttgccaag ttcgcattcg   1200
cgttcggtga tccgaattcg agctccgtcg acaagcttgc ggccgcactc gagcaccacc   1260
accaccacca ctgagatccg gctgctaaca aagcccgaaa ggaagctgag ttggctgctg   1320
ccaccgctga gcaataacta a                                              1341
```

<210> SEQ ID NO 34
<211> LENGTH: 276
<212> TYPE: PRT
<213> ORGANISM: Artificial Sequence
<220> FEATURE:
<223> OTHER INFORMATION: Amino acid sequence of the "4C" construct
      (123-amino-acid truncated dehalogenase/D2A21' trimer fusion).

<400> SEQUENCE: 34

```
Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Ser His Arg Cys Ile Ala Pro
        50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Gly Gln Gln Met Gly
        115                 120                 125

Arg Asp Pro Phe Ala Lys Lys Phe Ala Lys Lys Phe Lys Lys Phe Ala
    130                 135                 140

Lys Lys Phe Ala Lys Phe Ala Phe Ala Phe Gly Asp Pro Phe Ala Lys
145                 150                 155                 160

Lys Phe Ala Lys Lys Phe Lys Lys Phe Ala Lys Lys Phe Ala Lys Phe
                165                 170                 175

Ala Phe Ala Phe Gly Asp Pro Phe Ala Lys Lys Phe Ala Lys Lys Phe
            180                 185                 190

Lys Lys Phe Ala Lys Lys Phe Ala Lys Phe Ala Phe Ala Phe Gly Asp
        195                 200                 205

Pro Ser Arg Arg Ser Leu Arg Lys Ser Ser Arg Asn Leu Pro Arg Ser
    210                 215                 220

Leu Pro Ser Ser His Ser Arg Ser Val Ile Arg Ile Arg Ala Pro Ser
```

```
225                 230                 235                 240
Thr Ser Leu Arg Pro His Ser Ser Thr Thr Thr Thr Thr Glu Ile
                245                 250                 255
Arg Leu Leu Thr Lys Pro Glu Arg Lys Leu Ser Trp Leu Leu Pro Pro
            260                 265                 270
Leu Ser Asn Asn
        275

<210> SEQ ID NO 35
<211> LENGTH: 831
<212> TYPE: DNA
<213> ORGANISM: Artificial Sequence
<220> FEATURE:
<223> OTHER INFORMATION: DNA sequence used to encode the "4C" construct
      (in P. fluorescens expression vector pMYC1803 and E. coli
      expression vector pET21b).

<400> SEQUENCE: 35
atgtcagaaa tcggtacagg cttccccttc gaccccatt atgtggaagt cctgggcgag      60
cgtatgcact acgtcgatgt tggaccgcgg gatggcacgc ctgtgctgtt cctgcacggt     120
aacccgacct cgtcctacct gtggcgcaac atcatcccgc atgtagcacc gagtcatcgg     180
tgcattgctc cagacctgat cgggatggga aaatcggaca aaccagacct cgattatttc     240
ttcgacgacc acgtccgcta cctcgatgcc ttcatcgaag ccttgggttt ggaagaggtc     300
gtcctggtca tccacgactg gggctcagct ctcggattcc actgggccaa gcgcaatccg     360
gaacgggtcg acagcaaat gggtcgggat ccgttcgcga agaagtttgc gaaaaagttc     420
aagaaatttg ccaagaagtt tgccaagttc gcattcgcgt tcggcgatcc gttcgcgaag     480
aagtttgcga aaaagttcaa gaatttgcca agaagtttg ccaagttcgc attcgcgttc     540
ggcgatccgt tcgcgaagaa gtttgcgaaa agttcaaga atttgccaa gaagtttgcc     600 aagttcgcat tcgcgttcgg cgatccttcg aagaagttt gcgaaaaag ttcaagaaat     660 ttgccaagaa gtttgccaag ttcgcattcg cgttcggtga tccgaattcg agctccgtcg     720
acaagcttgc ggccgcactc gagcaccacc accaccacca ctgagatccg gctgctaaca     780
aagcccgaaa ggaagctgag ttggctgctg ccaccgctga gcaataacta a             831

<210> SEQ ID NO 36
<211> LENGTH: 801
<212> TYPE: DNA
<213> ORGANISM: Artificial Sequence
<220> FEATURE:
<223> OTHER INFORMATION: DNA sequence encoding the 16A (D2A21) trimer
      (in P. fluorescens expression vector pMYC1803).

<400> SEQUENCE: 36
atgtcagaaa tcggtacagg cttccccttc gaccccatt atgtggaagt cctgggcgag      60
cgtatgcact acgtcgatgt tggaccgcgg gatggcacgc ctgtgttgtt cctgcacggt     120
aacccgacct cgtcctacct gtggcgcaac atcatcccgc atgtagcacc gagtcatcgg     180
tgcattgctc cagacctgat cgggatggga aaatcggaca aaccagacct cgattatttc     240
ttcgacgacc acgtccgcta cctcgatgcc ttcatcgaag ccttgggttt ggaagaggtc     300
gtcctggtca tccacgactg gggctcagct ctcggattcc actgggccaa gcgcaatccg     360
gaacgggtca tggctagcat gactggtgga cagcaaatgg gtcgggatcc gttcaaactg     420
cgtgctaaaa tcaagttcg tctgcgtgct aaaatcaaac tgggtgaccc tgatccgttc     480
aaactgcgtg ctaaaatcaa agttcgtctg cgtgctaaaa tcaaactggg tgaccctgat     540
```

```
ccgttcaaac tgcgtgctaa atcaaagtt cgtctgcgtg ctaaaatcaa actgggtgac    600
cctgatccgt tcaaactgcg tgctaaaatc aaagttcgtc tgcgtgctaa atcaaactg    660 ggtgaccctg atccgttcaa actgcgtgct aaaatcaaag ttcgtctgcg tgctaaaatc    720
aaactgggtg accctgatcc gaattcgagc tccgtcgaca agcttgcggc cgcactcgag    780
caccaccacc accaccactg a                                              801
```

```
<210> SEQ ID NO 37
<211> LENGTH: 140
<212> TYPE: PRT
<213> ORGANISM: Artificial Sequence
<220> FEATURE:
<223> OTHER INFORMATION: Amino acid sequence of the 16A (D2A21) trimer.

<400> SEQUENCE: 37
```

```
Met Ala Ser Met Gly Arg Asp Pro Phe Ala Lys Lys Phe Ala Lys Lys
1               5                   10                  15

Phe Lys Lys Phe Ala Lys Lys Phe Ala Lys Phe Ala Phe Ala Phe Gly
                20                  25                  30

Asp Pro Phe Ala Lys Lys Phe Ala Lys Lys Phe Ala Lys Lys Phe Ala Lys
            35                  40                  45

Lys Phe Ala Lys Phe Ala Phe Ala Phe Gly Asp Pro Phe Ala Lys Lys
        50                  55                  60

Phe Ala Lys Lys Phe Ala Lys Lys Phe Ala Lys Lys Phe Ala Lys Phe Ala
65                  70                  75                  80

Phe Ala Phe Gly Asp Pro Ser Arg Arg Ser Leu Arg Lys Ser Ser Arg
                85                  90                  95

Asn Leu Pro Arg Ser Leu Pro Ser Ser His Ser Arg Ser Val Ile Arg
            100                 105                 110

Ile Arg Ala Pro Ser Asn Thr Arg Ala Gln Asn Glu Arg Leu Ser Arg
        115                 120                 125

Gln Thr Gly Pro Phe Val Leu Ser Val Val Cys Arg
    130                 135                 140
```

```
<210> SEQ ID NO 38
<211> LENGTH: 411
<212> TYPE: DNA
<213> ORGANISM: Artificial Sequence
<220> FEATURE:
<223> OTHER INFORMATION: DNA sequence encoding the 21A (D2A21) trimer
      (in P. fluorescens expression vector pMYC1803).

<400> SEQUENCE: 38
```

```
atgggtcggg atccgttcgc gaagaagttt gcgaaaaagt tcaagaaatt tgccaagaag     60
tttgccaagt tcgcattcgc gttcggcgat ccgttcgcga agaagtttgc gaaaaagttc    120
aagaaatttg ccaagaagtt tgccaagttc gcattcgcgt tcggcgatcc gttcgcgaag    180
aagtttgcga aaaagttcaa gaaatttgcc aagaagtttg ccaagttcgc attcgcgttc    240
ggcgatcctt cgcgaagaag tttgcgaaaa agttcaagaa atttgccaag aagtttgcca    300
agttcgcatt cgcgttcggt gatccgaatt cgagctccgt ctaatactcg agcccaaaac    360
gaaaggctca gtcgacagac tgggcctttc gttttatctg ttgtttgtcg g             411
```

```
<210> SEQ ID NO 39
<211> LENGTH: 137
<212> TYPE: PRT
<213> ORGANISM: Artificial Sequence
<220> FEATURE:
```

<223> OTHER INFORMATION: Amino acid sequence of the 21A (D2A21) trimer.

<400> SEQUENCE: 39

```
Met Gly Arg Asp Pro Phe Ala Lys Lys Phe Ala Lys Lys Phe Lys Lys
1               5                   10                  15

Phe Ala Lys Lys Phe Ala Lys Phe Ala Phe Gly Asp Pro Phe
                20                  25                  30

Ala Lys Lys Phe Ala Lys Lys Phe Lys Lys Phe Ala Lys Lys Phe Ala
                35                  40                  45

Lys Phe Ala Phe Ala Phe Gly Asp Pro Phe Ala Lys Lys Phe Ala Lys
                50                  55                  60

Lys Phe Lys Lys Phe Ala Lys Lys Phe Ala Lys Phe Ala Phe Ala Phe
65                  70                  75                  80

Gly Asp Pro Ser Arg Arg Ser Leu Arg Lys Ser Ser Arg Asn Leu Pro
                85                  90                  95

Arg Ser Leu Pro Ser Ser His Ser Arg Ser Val Ile Arg Ile Arg Ala
                100                 105                 110

Pro Ser Asn Thr Arg Ala Gln Asn Glu Arg Leu Ser Arg Gln Thr Gly
                115                 120                 125

Pro Phe Val Leu Ser Val Val Cys Arg
                130                 135
```

<210> SEQ ID NO 40
<211> LENGTH: 420
<212> TYPE: DNA
<213> ORGANISM: Artificial Sequence
<220> FEATURE:
<223> OTHER INFORMATION: DNA sequence encoding the 21B (D2A21) trimer
      (in P. fluorescens expression vector pMYC1803).

<400> SEQUENCE: 40

```
atggctagca tgggtcggga tccgttcgcg aagaagtttg cgaaaaagtt caagaaattt    60
gccaagaagt ttgccaagtt cgcattcgcg ttcggcgatc cgttcgcgaa gaagtttgcg   120
aaaaagttca gaaatttgc caagaagttt gccaagttcg cattcgcgtt cggcgatccg   180
ttcgcgaaga agtttgcgaa aaagttcaag aaatttgcca gaagtttgc caagttcgca   240 ttcgcgttcg gcgatccttc gcgaagaagt tgcgaaaaa gttcaagaaa tttgccaaga   300
agtttgccaa gttcgcattc gcgttcggtg atccgaattc gagctccgtc taatactcga   360
gcccaaaacg aaaggctcag tcgacagact gggcctttcg ttttatctgt tgtttgtcgg   420
```

<210> SEQ ID NO 41
<211> LENGTH: 140
<212> TYPE: PRT
<213> ORGANISM: Artificial Sequence
<220> FEATURE:
<223> OTHER INFORMATION: Amino acid sequence of the 21B (D2A21) trimer.

<400> SEQUENCE: 41

```
Met Ala Ser Met Gly Arg Asp Pro Phe Ala Lys Lys Phe Ala Lys Lys
1               5                   10                  15

Phe Lys Lys Phe Ala Lys Lys Phe Ala Lys Phe Ala Phe Ala Phe Gly
                20                  25                  30

Asp Pro Phe Ala Lys Lys Phe Ala Lys Lys Phe Lys Lys Phe Ala Lys
                35                  40                  45

Lys Phe Ala Lys Phe Ala Phe Ala Phe Gly Asp Pro Phe Ala Lys Lys
                50                  55                  60

Phe Ala Lys Lys Phe Lys Lys Phe Ala Lys Lys Phe Ala Lys Phe Ala
```

```
                65                  70                  75                  80
Phe Ala Phe Gly Asp Pro Ser Arg Arg Ser Leu Arg Lys Ser Ser Arg
                    85                  90                  95

Asn Leu Pro Arg Ser Leu Pro Ser Ser His Ser Arg Ser Val Ile Arg
                100                 105                 110

Ile Arg Ala Pro Ser Asn Thr Arg Ala Gln Asn Glu Arg Leu Ser Arg
        115                 120                 125

Gln Thr Gly Pro Phe Val Leu Ser Val Val Cys Arg
    130                 135                 140

<210> SEQ ID NO 42
<211> LENGTH: 168
<212> TYPE: DNA
<213> ORGANISM: Artificial Sequence
<220> FEATURE:
<223> OTHER INFORMATION: DNA sequence encoding the JP2 (D2A21) dimer
      (in P. fluorescens expression vector pMYC1803).

<400> SEQUENCE: 42
atggcggatc cgttcgcgaa gaagtttgcg aaaaagttca gaaatttgc caagaagttt     60 gccaagttcg cattcgcgtt cggcgatccg ttcgcgaaga gtttgcgaa aaagttcaag    120 aaatttgcca gaagtttgc caagttcgca ttcgcgttcg gcgattaa                 168

<210> SEQ ID NO 43
<211> LENGTH: 55
<212> TYPE: PRT
<213> ORGANISM: Artificial Sequence
<220> FEATURE:
<223> OTHER INFORMATION: JP2 amino acid sequence of the D2A21 dimer in
      P.f. expression vector, pMYC1803.

<400> SEQUENCE: 43

Met Ala Asp Pro Phe Ala Lys Lys Phe Ala Lys Lys Phe Lys Lys Phe
1               5                   10                  15

Ala Lys Lys Phe Ala Lys Phe Ala Phe Ala Phe Gly Asp Pro Phe Ala
                20                  25                  30

Lys Lys Phe Ala Lys Lys Phe Lys Lys Phe Ala Lys Lys Phe Ala Lys
            35                  40                  45

Phe Ala Phe Ala Phe Gly Asp
        50                  55

<210> SEQ ID NO 44
<211> LENGTH: 266
<212> TYPE: PRT
<213> ORGANISM: Artificial Sequence
<220> FEATURE:
<223> OTHER INFORMATION: Amino acid sequence of the truncated
      dehalogenase/D4E1 pentamer fusion.

<400> SEQUENCE: 44

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Ser His Arg Cys Ile Ala Pro
        50                  55                  60

Asp Leu Ile Gly Met Gly Lys Ser Asp Lys Pro Asp Leu Asp Tyr Phe
65                  70                  75                  80
```

Phe Asp Asp His Val Arg Tyr Leu Asp Ala Phe Ile Glu Ala Leu Gly
            85                  90                  95

Leu Glu Glu Val Val Leu Val Ile His Asp Trp Gly Ser Ala Leu Gly
        100                 105                 110

Phe His Trp Ala Lys Arg Asn Pro Glu Arg Val Met Ala Ser Met Thr
    115                 120                 125

Gly Gly Gln Gln Met Gly Arg Asp Pro Phe Lys Leu Arg Ala Lys Ile
130                 135                 140

Lys Val Arg Leu Arg Ala Lys Ile Lys Leu Gly Asp Pro Asp Pro Phe
145                 150                 155                 160

Lys Leu Arg Ala Lys Ile Lys Val Arg Leu Arg Ala Lys Ile Lys Leu
            165                 170                 175

Gly Asp Pro Asp Pro Phe Lys Leu Arg Ala Lys Ile Lys Val Arg Leu
            180                 185                 190

Arg Ala Lys Ile Lys Leu Gly Asp Pro Asp Pro Phe Lys Leu Arg Ala
        195                 200                 205

Lys Ile Lys Val Arg Leu Arg Ala Lys Ile Lys Leu Gly Asp Pro Asp
210                 215                 220

Pro Phe Lys Leu Arg Ala Lys Ile Lys Val Arg Leu Arg Ala Lys Ile
225                 230                 235                 240

Lys Leu Gly Asp Pro Asp Pro Asn Ser Ser Ser Val Asp Lys Leu Ala
            245                 250                 255

Ala Ala Leu Glu His His His His His His
            260                 265

<210> SEQ ID NO 45
<211> LENGTH: 801
<212> TYPE: DNA
<213> ORGANISM: Artificial Sequence
<220> FEATURE:
<223> OTHER INFORMATION: DNA sequence encoding the fusion protein of
      SEQ ID NO:44 (in P. fluorescens expression vector pMYC1803).

<400> SEQUENCE: 45
atgtcagaaa tcggtacagg cttcccttc gaccccatt atgtggaagt cctgggcgag      60
cgtatgcact acgtcgatgt tggaccgcgg gatggcacgc ctgtgttgtt cctgcacggt     120
aacccgacct cgtcctacct gtggcgcaac atcatcccgc atgtagcacc gagtcatcgg     180
tgcattgctc cagacctgat cgggatggga aaatcggaca accagacct cgattatttc     240 ttcgacgacc acgtccgcta cctcgatgcc ttcatcgaag ccttgggttt ggaagaggtc     300
gtcctggtca tccacgactg gggctcagct ctcggattcc actgggccaa gcgcaatccg     360
gaacgggtca tggctagcat gactggtgga cagcaaatgg gtcgggatcc gttcaaactg     420
cgtgctaaaa tcaaagttcg tctgcgtgct aaaatcaaac tgggtgaccc tgatccgttc     480
aaactgcgtg ctaaaatcaa agttcgtctg cgtgctaaaa tcaaactggg tgaccctgat     540
ccgttcaaac tgcgtgctaa atcaaagtt cgtctgcgtg ctaaaatcaa actgggtgac     600
cctgatccgt tcaaactgcg tgctaaaatc aaagttcgtc tgcgtgctaa atcaaactg     660 ggtgacccta tccgttcaa actgcgtgct aaaatcaaag ttcgtctgcg tgctaaaatc     720
aaactgggtg accctgatcc gaattcgagc tccgtcgaca agcttgcggc cgcactcgag     780
caccaccacc accaccactg a                                               801

LOW-COST PRODUCTION OF PEPTIDES

CROSS REFERENCE TO RELATED APPLICATIONS

This application is a continuation of International Application No. PCT/US03/12407, filed Apr. 22, 2003, which claims priority to U.S. Provisional Application No. 60/374,644, filed on Apr. 22, 2002.

BACKGROUND

Various proteins and peptides are useful and valuable for human-health (and other) purposes. For example, there is a broad class of anti-microbial peptides (AMPs) that have, by definition, antibiotic properties. These peptides have the potential for broad use as therapeutics, anti-infectives, disinfectants, and preservatives—if they could be economically produced.

Other types of small peptides include hormones, which also have a wide range of therapeutic uses.

Antimicrobial peptides are natural components of natural antimicrobial defenses of many types of organisms, including mammals, birds, reptiles, insects, and plants. There are many types of antimicrobial peptides, and there are many natural sources of these peptides. Many classes of natural AMPs have been named. For example there are magainins from frogs (See e.g. Zasloff et al. (1987)); attacins and cecropins from silk moths (See e.g. Bowman et al. (1983)); defensins from rabbits, humans, and other mammals (See e.g. Pardi et al. (1992)); indolicidins and bacteriocins from cows (See e.g. Selsted et al. (1992) and Niidome et al. (1999)); and apidaecins from honeybees (See e.g. Casteels et al. (1989)). See also WO 00/31729.

In addition, AMPs are produced by Arthropods (crabs, shrimp, horseshoe crabs, spiders, scorpions) and lower invertebrates (earthworms, mollusks and sponges). Microorganisms also produce AMPs, including myxobacteria, actinomycetes, eubacteria, fungi (both Ascomycetes and Basidiomycetes), and protists such as amoeba. See Table 1.

TABLE 1

| Author and Year | Citation | Group of Organisms |
| --- | --- | --- |
| (1999) | JP 2854872 B2 | Horseshoe Crabs |
| Aszodi et al. (1999) | U.S. Pat. No. 5,891,851 (Hoechst AG) | Actinomycetes |
| Bachere et al. (1999) | WO 99/05270 A2 | Shrimp |
| Bowman et (1983) | The EMBO Journal 2: 571-576 | Silk Moths, Attacins and Cecropins |
| Casteels et al. (1989) | The EMBO Journal 8: 2387-2391 | Honeybees, Apidaecins |
| Cho et al. (1998) | Biochimica et Biophysica Acta 1480: 67-76 | Annelids |
| Gulavita et al. (1996) | U.S. Pat. No. 5,516,755 (Harbor Branch Oceanographic Institution) | Sponges |
| Haeberli et al. (2000) | Toxicon 38: 373-380 | Spiders |
| Hetru et al. (2000) | Biochemical Journal J 345: 653-664 | Scorpions |
| Iwanaga et al. (1998) | Frontiers in Bioscience 3: D973-84 | Crabs |
| Leippe et al. (1999) | Developmental and Comparative Immunology 23: 267-79 | Amoebae |
| Logeman et al. (1991) | EP 525508 A2 (Max Planck Institute) | Basidiomycetes |
| Mitta et al. (1999) | Journal of Cell Science 112: 4233-4242 | Molusks |
| Niidome et al. (1999) | Peptide Science 36: 403-406 | Cows, Bactenecins |
| Pardi et al. (1992) | Biochemistry 31: 11357-11364 | Rabbits and Humans, Defensins |
| Ryals et al. (1998) | U.S. Pat. No. 5,716,849 (Novartis) | Myxobacteria |
| Selsted et al. (1992) | J. Biological Chemistry 267: 4292-4295 | Mammals, Indolicidins |
| Ulbrich et al. (1998) | U.S. Pat. No. 5,824,874 (Hoechst) | Ascomycetes |
| Zasloff et al. (1987) | PNAS 84: 5449-5453 | Frogs, Magainins |

Some AMPs and structurally similar peptides have been found to have selective activity against cancer cells. See e.g. WO 97/33908 (CSIRO) and WO 90/12866 (Louisiana State University). It has also been possible to synthesize man-made AMP and anti-tumor peptide sequences by modifications of natural analogs (see e.g. U.S. Pat. No. 5,994,306; Intrabiotics), by design from general principles of peptide structure/activity relationships (see e.g. U.S. Pat. No. 5,861,478; Helix Biomedix), or even by screening of random combinations (see e.g. U.S. Pat. No. 5,504,190; Torrey Pines Institute).

Typical AMPs are approximately 10 to 50 amino acids in length. These peptides tend to be relatively rich in basic amino acids (lysine and arginine) and thus tend to be cationic (having a net positive charge). AMPs are amphipathic in nature (i.e., one part of the molecule is hydrophilic while the other part is hydrophobic). Though widely studied, the mode of action of AMPs remains a subject of scientific debate. In many cases the data suggests that the amphipathic peptides organize to form pores or channels in membranes. See e.g. Durell et al. (1992), *Biophysical Journal* 63:1623-1631. In other cases the AMPs appear to disrupt a membrane by forming a "carpet-like" association with the membrane. See e.g. Shai et al. (1995), *Biochemistry* 34:11479-88. This disrupts and kills microbes by causing cellular membrane depolarization and the loss of essential cellular components.

AMPs have broad-spectrum antimicrobial activities; this is one attractive aspect of using AMPs as pharmaceutical antibiotics. In light of the increasingly widespread appearance of pathogenic microbes that are resistant to a range of typical chemical antibiotics, there is interest in using antimicrobial peptides (AMPs) as an alternative to typical chemical antibiotics if they could be economically produced.

AMPs have the potential for broad use as therapeutics (see e.g. U.S. Pat. No. 6,132,775; New York University), anti-infectives (see e.g. U.S. Pat. No. 6,071,879; University of Oklahoma), disinfectants (see e.g. Jaynes et al. [1996], *CLAO J.* 22:114-7), preservatives (see e.g. WO 00/01400; Assoc. Cape Cod Inc), and for food safety (see e.g. Padgett et al. [1998], *Journal of Food Protection* 61:1330-1335). AMPs and AMP-like peptides are also of interest for therapeutic uses against cancer and viruses (see e.g. Egal et al. [1999], *International Journal of Antimicrobial Agents* 13:57-60), including retro-viruses (see e.g. Tamamura et al. [1998], *Bioorganic and Medicinal Chemistry* 6:231-238). There is also considerable interest in using AMPs for the control of plant diseases, primarily through using transgenic plant approaches. See, e.g., Norelli et al. (1999), *Phytopathology* 89:S56.

However, a practical limitation to large-scale therapeutic and related uses of AMPs or other short peptide sequences is that they are expensive (and difficult/inefficient) to produce in mass quantities. For example, chemical peptide synthesis of AMPs (and other peptides or proteins) is very costly.

The synthetic production of heterologous proteins of therapeutic or functional (e.g., catalytic) significance in microorganisms has been attained. See e.g. Swartz, J. R. (2001), *Current Opinion in Biotechnology* 12:195-201. Such methods of producing polypeptides have the potential for providing some advantages over solid phase synthesis, including sequence fidelity, convenience, low cost, and the ability to produce long polypeptides/proteins. While microbial production of certain types of proteins and polypeptides can be convenient and cost-effective, such techniques cannot be universally applied, and limitations are often evident. These limitations can include: 1) low yield, 2) accumulation of misfolded and inactive protein, 3) inhibition of microbial growth, and 4) difficulties with detection or isolation/purification of polypeptides, particularly those of low molecular weight.

Attempts have been made to biologically produce small peptides as part of larger fusion proteins to improve overall protein yield. For example, U.S. Pat. Nos. 6,242,219 and 6,274,344 (Xoma Corp.) relate to a peptide derived from a bactericidal/permeability-increasing protein (BPI) fused to (and cleavable from) a carrier protein. The '219 patent relates to simultaneous acid lysis and cleavage of the peptide from the carrier. Asp-Pro linkage can be used between the peptide and the carrier. The '344 patent indicates that it might be possible for the carrier to be cationic, like the BPI.

Small peptides are quite susceptible to degradation by native proteases in bacteria. Small peptides, including AMPs, may be produced in nature as part of a multipeptide precursor. Casteels-Josson et al. (1993), *EMBO Journal,* 12(4):1569-1578. Insect neuropeptides (short peptides) appear to be produced naturally in a like manner. See, e.g., Rao et al. (1996), *Gene* 17:1-5. However, it can be quite difficult to replicate natural events in vitro. For example, assembling and expressing multiple copies of a desired DNA fragment in an easily cleavable manner can be a laborious and costly process. For background on amplifying multiple copies of cloned DNA segments, more generally, see e.g. Cohen et al. (1986), *DNA* 5(4):334-345, which relates to the use of tandem repeats of DNA fragments to produce multimers having inverted repeat structures (polyoma virus DNA was used as the monomer); and Kim et al. (1988), *Gene,* 71:1-8, which relates to the amplification of cloned DNA as tandem multimers (wherein the monomers have asymmetric cohesive ends).

Thus, there are hurdles to the synthetic production of small peptides, and AMPs are particularly difficult to synthesize biologically. In addition to being short and subject to proteolytic degradation, AMPs are, by definition, toxic to bacteria and other microbes. Thus, production of them in bioreactors as native, active material is practically precluded. Furthermore, AMPs tend to be positively charged/cationic, which presents other obstacles to synthetic biological production as explained in more detail below.

Recombinant *E. coli,* for example, have been used in attempts to biosynthetically produce AMPs. However, the yields (heretofore), if any, have been extremely low. By definition, AMPs are toxic to bacteria and other microorganisms. Thus, when any significant amount of AMP is produced by a culture (of *E. coli,* for example), the AMPs tend to kill the cultures. U.S. Pat. No. 5,206,154 (Xoma Corporation) claims a cecropin fused to a carrier (araB) in an effort to suppress the activity of the cecropin. If this approach was successful, the relative yield of the AMP, relative to the carrier, would be low.

Attempts have also been made to synthetically produce AMPs by first producing them as a multimeric/concatemeric precursor that is later cleaved to yield the active monomers. However, there were also problems with producing AMPs in that manner.

Attempting to produce AMPs as a multipeptide precursor poses unique, especially difficult problems with biological synthesis. More specifically, because of the highly cationic/positive charge of a single AMP, creating a multimeric protein comprising a plurality of AMP monomers is essentially creating a larger, highly cationic protein. It has been proposed that the positive charge of the nascent AMP multimer (which is cationic due to the abundance of basic amino acid residues in the AMPs), interacts with the negative charge of the DNA and/or RNA (which are acidic) involved in transcription and translation, thereby disrupting natural cellular processes and preventing production of the desired AMP to any substantial level. See, e.g., Lee et al. (1996), *Genetic Analysis: Biomolecular Engineering,* 13:139-145 (relating to the amplification of constructs comprising tandem multimers of 93 base-pair magainin monomers; it is proposed therein that positively charged amino acids of the polymer should be neutralized by fusing the polymer to a negatively charged protein). Protease degradation of product peptides is another observed problem.

Various attempts have been made to produce AMPs in the form of fusion proteins in which the positive charge of the AMP is balanced or neutralized by a carrier protein. WO 96/28559 (University of British Columbia; Hancock et al.) relates to a fusion protein having an anionic AMP portion and a cationic/LPS-binding portion that is said to suppress the anti-microbial activity of the cationic portion.

U.S. Pat. No. 5,593,866 (University of British Columbia) describes the use of a cationic/anionic fusion in an attempt to biosynthetically produce AMPs. This patent discloses a cecropin/melittin fusion comprising the first 18 amino acids of cecropin and the last 8 amino acids of melittin. Examples of the carrier peptides described therein include the GST protein from *S. aureus* and an outer membrane protein, protein F, from *P. aeruginosa.* Cyanogen bromide was used to cleave the fusion to recover active peptides. This patent claims the use of *Escherichia coli*, *Staphylococcus aureus*, and *Pseudomonas aeruginosa* for producing the fusion protein. This patent also states that the AMP of that invention can be used to inhibit *E. coli*, *P. aeruginosa*, *E. cloacae*, *S. typhimurium*, and *S. aureus*. This patent also relates to an AMP having two additional lysine residues on the carboxy terminus; this was reported to have surprisingly doubled the antimicrobial activity of the AMP.

Lee et al. (1998), *J. Microbiol. Biotechnol.*, 8(1):34-41, use a maltose-binding protein fused to magainin multimers in an attempt to achieve adequate expression. They used Factor Xa cleavage sites between the monomers. This reference stated that the AMPs resulting from the Factor Xa cleavage surprisingly retained activity despite having additional amino acid residues on the core AMP.

Lee et al. (February 1998; *Protein Expression and Purification, vol.* 12, no. 1, pp. 53-60) use tandem repeats of an acidic peptide fused to the basic/positively charged AMP (buforin II). A cysteine residue was added as a critical element to each end of the acidic peptide. Cyanogen bromide was the cleavage agent used therein.

Lee et al. (June 1999), *J. Microbiol. and Biotech.*, 9(3):303-310, use a buforin II AMP fused to a cysteine-rich acidic peptide. Zhang et al. (1998), *Biochemical and Biophysical Research Communications*, 247:674-680, relates to fusion proteins comprising a cecropin/magainin and a carrier protein comprising an anionic prepro domain, a RepA domain, and a cellulose-binding domain.

WO 98/54336 (Kim, Lee, et al.; Samyang Genex and Korea Advanced Institute Science; see also U.S. Pat. No. 6,183,992) relates to the use of a fusion of an AMP (Buforin II) with an acidic peptide (Guamerin) that has at least two cysteine residues. This application teaches that the acidic peptide is required to neutralize the basic/positively charged AMP in order to prevent electrical attractions and interactions with DNA and RNA during translation of the AMP. The cysteine residues are also taught to be necessary to facilitate the interaction and proper folding of the two portions of the polypeptide. WO 98/54336 distinguishes U.S. Pat. No. 5,593,866 by stating that a general acidic carrier peptide gene alone does not permit an efficient expression of a basic antimicrobial peptide; the presence of at least two cysteine residues in the acidic peptide is also needed to efficiently solve the problem. WO 98/54336 similarly describes WO 96/28559 as being inoperative and likewise suggests the use of cysteine residues in the anionic peptide as the solution to the problem.

WO 99/64611 (Samyang Genex Corp.) relates to the use of fusions comprising a purF gene and an AMP. Another Samyang Genex application, WO 00/34312, relates to the use of hydroxylamine for cleaving a basic peptide/protein from a fusion partner. U.S. Pat. No. 6,255,279 and WO 99/48912 (Korea Advanced Institute) mention the possible use of an AMP in mouthwashes and eyewashes. WO 97/22624 (Beiersdorf AG) relates to the use of random multimers for use in an antimicrobial cosmetic preparations, deodorants, and the like.

WO 00/31279 (Micrologix Biotech Inc.) relates to a "multi-domain fusion protein," which appears to be a multimeric AMP fused to an acidic peptide (a cellulose-binding domain) wherein there are, as an essential element, anionic spacers between each AMP monomer for "charge balancing" (i.e., to eliminate the charge of the cationic peptide component). This application uses small spacers (that provide a concentrated negative charge) to raise the relative production of the AMPs as compared to total protein produced by the cell; this type of multimer can itself be fused to a carrier protein (a cellulose-binding domain). Although this application briefly mentions that 70% formic acid might be a possible cleavage agent, cyanogen bromide (CNBr) is exemplified throughout this application to cleave (at methionine residues) the multi-domain protein to yield active monomers. WO 00/31279 states that the fusion protein can be an insoluble protein. An "insoluble peptide" is defined therein as "a polypeptide that, when cells are broken open and cellular debris precipitated by centrifugation (e.g., 10,000×g to 15,000×g), produces substantially no soluble component, as determined by SDS polyacrylamide gel with Coomassie Blue staining."

There has been no suggestion in the art that *Pseudomonas fluorescens* (*P. fluorescens*) would be advantageous for or capable of producing AMPs.

*Pseudomonas aeruginosa* and *P. fluorescens* have been used commercially for the production of Vitamin $B_{12}$. See Schenectady County Community College website. Certain strains of *P. fluorescens* are known to have anti-fungal properties. See, e.g., U.S. Pat. No. 6,048,713. Some strains of *P. fluorescens* are known to produce antibiotics and can be used in the production of these antibiotics. See, e.g., U.S. Pat. No. 4,108,724. See also U.S. Pat. No. 5,348,742. The use of *P. fluorescens* to produce insecticidal protein toxins is also known. See, e.g., U.S. Pat. Nos. 5,840,554; 5,527,883; 5,128,130; and 5,055,294 (Mycogen Corporation). *P. fluorescens* has also been used for bioremediation of environmental contamination. See, e.g., U.S. Pat. Nos. 5,711,945 and 4,853,334.

In all of these peptide expression systems, the yield of polypeptide expressed from the transgene in the cell culture is typically reported in the range from a few micrograms per liter to about 100 mg/L. As a result, there is still a need in the art for transgenic polypeptide expression systems that provide significantly higher yields. Thus, there is a long-felt and critical need for methods of producing small peptides, including AMPs, in efficient, cost-effective manners using microbial fermentation.

SUMMARY

A process for biosynthetic production of small peptides, said process including: Providing at least one microbial cell; and at least one nucleic acid from which said microbial cell can express a carrier-peptide fusion polypeptide containing (a) at least one highly expressed carrier polypeptide linked by a cleavable linker to (b) at least one peptide multimer, the peptide multimer containing at least two small peptide units in tandem arrangement, each small peptide unit being linked to at least one adjacent small peptide unit by a cleavage site containing at least one Asp-Pro dipeptide; transfecting said nucleic acid into said microbial cell to obtain a transformed microbial cell; placing said transformed microbial cell in conditions in which the cell can express the nucleic acid to produce the carrier-peptide fusion polypeptide encoded thereby; optionally, recovering said carrier-peptide fusion polypeptide from the transformed microbial cell; optionally, performing a cleavage reaction to cleave said carrier polypeptide(s) from said peptide multimer; performing a cleavage reaction to cleave the small peptide units of the multimer from one another, thereby obtaining small peptides; and optionally, performing a terminal cleavage reaction to remove cleavage site amino acid residues, or cleavable linker amino acid residues, or both, that are present at a terminus or termini of the small peptides.

The process wherein said microbial cell is a bacterial cell. The process wherein said bacterial cell is a member of the gamma Proteobacteria. The process wherein said bacterial cell is a member of the genus *Pseudomonas*. The process wherein said bacterial cell is a member of the *Pseudomonas fluorescens* group. The process wherein said bacterial cell is *Pseudomonas fluorescens*. The process wherein said bacterial cell is *Pseudomonas fluorescens* biovar A.

The process wherein each of the cleavage site(s) linking the small peptide units together contains at least one Gly-Asp-Pro tripeptide. The process wherein each of the cleavage site(s) linking the small peptide units together is a Gly-Asp-Pro tripeptide. The process wherein the peptide multimer contains at least three peptide units in tandem arrangement. The process wherein each of the peptide unit is expressed in the same orientation within said peptide multimer. The process wherein the small peptide units of said peptide multimer have identical amino acid sequences. The process wherein said highly expressed carrier polypeptide is an N-terminal fragment of a protein that is highly expressed in the microbial cell. The process wherein said N-terminal fragment is about or at least 10 amino acid residues in length. The process wherein said protein is the *Rhodococcus rhodochrous* TDTM-003 haloalkane dehalogenase (SEQ ID NO:30).

A nucleic acid from which may be expressed a carrier-peptide fusion polypeptide containing (a) at least one highly expressed carrier polypeptide linked by a cleavable linker to (b) at least one peptide multimer, the peptide multimer containing at least two small peptide units in tandem arrangement, each small peptide unit being linked to at least one adjacent small peptide unit by a cleavage site containing at least one Asp-Pro dipeptide. The nucleic acid wherein said nucleic acid is a vector. The nucleic acid wherein said vector is a plasmid. The nucleic acid wherein said nucleic acid is prepared by a process involving annealing and ligation of oligomers, including pseudopalindromic oligomers, to form a pool of multimeric polynucleotides containing peptide unit-encoding oligonucleotides in tandem and linked by cleavage site-encoding nucleotides, said pool both containing multimeric polynucleotides whose peptide unit-encoding oligonucleotide portions are all arranged in the same orientation and multimeric polynucleotides whose peptide unit-encoding oligonucleotide portions are arranged in differing orientations, followed by treatment of the multimeric polynucleotides with appropriate restriction endonucleases so that the only multimeric polynucleotides that are hydrolyzed are those whose peptide unit-encoding oligonucleotide portions are arranged in differing orientations. A microbial cell containing the nucleic acid.

Small peptides are produced by the process. The small peptides can be anti-microbial peptides (AMPs).

BRIEF DESCRIPTION OF THE FIGURES

FIG. 3A shows a pseudopalindromic spacer strategy used to assemble correctly oriented genes (encoding AMPs linked with the Asp-Pro dipeptide) to form a multimer/concatamer. Ligation of cohesive ends of the genes in the desired orientation results in a nonpalindromic sequence which encodes the Asp-Pro dipeptide.

FIG. 3B shows palindromic sequences resulting from incorrect "head-to-head" or "tail-to-tail" ligations that can be cleaved by *Pvu*I.

FIG. 3C shows palindromic sequences resulting from incorrect "head-to-head" or "tail-to-tail" ligations that can be cleaved by *Bam*HI.

BRIEF DESCRIPTION OF THE SEQUENCES

Figure 1:
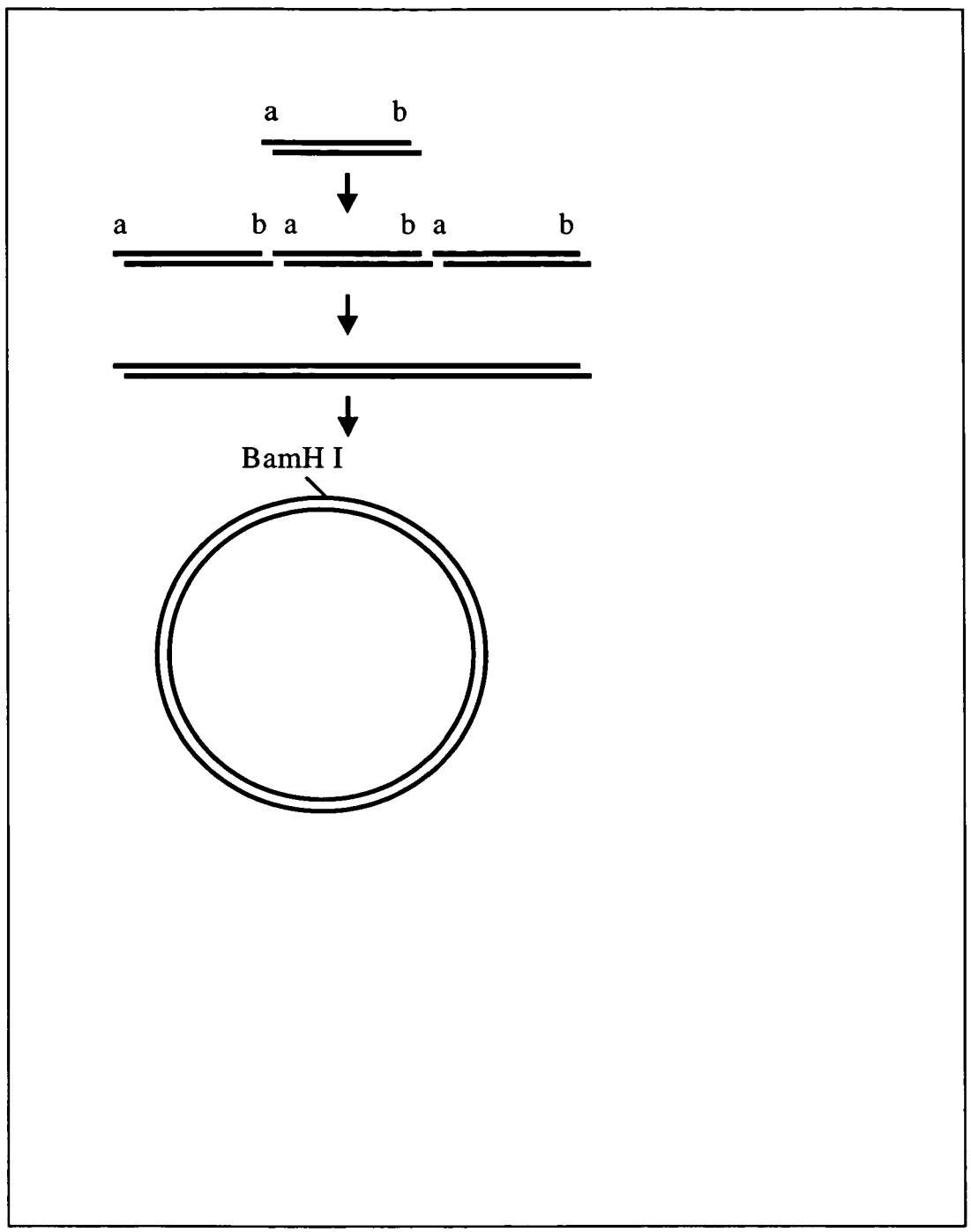
FIG. 1 illustrates an assembly of DNA segments that encode monomeric AMP subunits in the correct orientations into a multimeric construct and then into a plasmid, as discussed below.

SEQ ID NO:1 shows the amino acid sequence for the core D2A21 antimicrobial peptide.

SEQ ID NO:2 shows the DNA sequence used to encode the peptide of SEQ ID NO:1.

SEQ ID NO:3 shows the DNA sequence used to encode the peptide of SEQ ID NO:4.

SEQ ID NO:4 shows the amino acid sequence for the core D2A21 antimicrobial peptide monomer with three additional amino acid residues for peptide linkage/cleavage sites for assembling into a multimer.

SEQ ID NO:5 is the DNA sequence that was used to encode the 4A dimer of SEQ ID NO:6 (using *E. coli* expression vector pET21b).

SEQ ID NO:6 shows the amino acid sequence of the 4A dimer (comprising a leader segment, two AMPs separated by a tripeptide linker, and a trailer segment).

SEQ ID NO:7 shows the amino acid sequence of the D2A21' AMP monomer.

SEQ ID NO:8 is a preferred hexanucleotide sequence that encodes the Asp-Pro cleavable dipeptide linker.

SEQ ID NO:9 shows the amino acid sequence of the AB4 trimer (comprising a leader segment, three AMPs each separated by a tripeptide linker, and a trailer segment).

SEQ ID NO:10 is the DNA sequence that was used to encode the AB4 trimer of SEQ ID NO:9 (in *E. coli* expression vector pET21b).

SEQ ID NO:11 shows the amino acid sequence of the TF3 trimer.

SEQ ID NO:12 shows the DNA sequence that was used to encode the TF3 trimer of SEQ ID NO:11 (in *P. fluorescens* expression vector pMYC1803).

SEQ ID NO:13 is the amino acid sequence of the D4E1 AMP.

SEQ ID NO:14 is the amino acid sequence of a D4E1 trimer.

SEQ ID NO:15 is the DNA sequence used to encode the D4E1 trimer of SEQ ID NO:14 (in *P. fluorescens* expression vector pMYC1803 and *E. coli* expression vector pET24b).

SEQ ID NO:16 is the amino acid sequence of the D4E1 tetramer.

SEQ ID NO:17 is the DNA sequence used to encode the D4E1 tetramer of SEQ ID NO:16 (in *P. fluorescens* expression vector pMYC1803).

SEQ ID NO:18 is the amino acid sequence of the D4E1 pentamer.

SEQ ID NO:19 is the DNA sequence used to encode the D4E1 pentamer of SEQ ID NO:18 (in *P. fluorescens* expression vector pMYC1803 and *E. coli* expression vector pET24b).

SEQ ID NO:20 is the amino acid sequence of the dihydrofolate reductase (DHFR) protein.

SEQ ID NO:21 is the DNA sequence of the DHFR gene encoding the dehalogenase protein of SEQ ID NO:20 (in *P. fluorescens* expression vector pMYC1803).

SEQ ID NO:22 is the amino acid sequence of the DHFR/TF3 trimer fusion.

SEQ ID NO:23 is the DNA sequence used to encode the fusion of SEQ ID NO:22 (in *P. fluorescens* expression vector pMYC1803).

SEQ ID NO:24 is the amino acid sequence of the DHFR/D4E1 trimer fusion.

SEQ ID NO:25 is the DNA sequence used to encode the fusion of SEQ ID NO:24 (in *P. fluorescens* expression vector pMYC1803).

SEQ ID NO:26 is the amino acid sequence of the DHFR/D4E1 tetramer fusion.

SEQ ID NO:27 is the DNA sequence used to encode the fusion of SEQ ID NO:26 (in *P. fluorescens* expression vector pMYC1803).

SEQ ID NO:28 is the amino acid sequence of the DHFR/D4E1 pentamer fusion.

SEQ ID NO:29 is the DNA sequence used to encode the fusion of SEQ ID NO:28 (in *P. fluorescens* expression vector pMYC1803).

SEQ ID NO:30 is the amino acid sequence of the full-length dehalogenase protein.

SEQ ID NO:31 is the DNA sequence used to encode the dehalogenase protein of SEQ ID NO:30.

SEQ ID NO:32 is the amino acid sequence of the "3I" fusion (dehalogenase/D2A21' trimer).

SEQ ID NO:33 is the DNA sequence used to encode the "3I" fusion of SEQ ID NO:32 (in *P. fluorescens* expression vector pMYC1803 and *E. coli* expression vector pET21b).

SEQ ID NO:34 is the amino acid sequence of the "4C" construct (123-amino-acid truncated dehalogenase/D2A21' trimer fusion).

SEQ ID NO:35 is the DNA sequence used to encode the "4C" construct (in *P. fluorescens* expression vector pMYC1803 and *E. coli* expression vector pET21b).

SEQ ID NO:36 is the DNA sequence encoding of the 16A (D2A21) trimer (in *P. fluorescens* expression vector pMYC1803).

SEQ ID NO:37 is the amino acid sequence of the 16A (D2A21) trimer.

SEQ ID NO:38 is the DNA sequence encoding of the 21A (D2A21) trimer (in *P. fluorescens* expression vector pMYC1803).

SEQ ID NO:39 is the amino acid sequence of the 21A (D2A21) trimer.

SEQ ID NO:40 is the DNA sequence encoding of the 21B (D2A21) trimer (in *P. fluorescens* expression vector pMYC1803).

SEQ ID NO:41 is the amino acid sequence of the 21B (D2A21) trimer.

SEQ ID NO:42 is the DNA sequence encoding of the JP2 (D2A21) dimer (in *P. fluorescens* expression vector pMYC1803).

SEQ ID NO:43 is the amino acid sequence of the JP2 (D2A21) dimer.

SEQ ID NO:44 is the amino acid sequence of the truncated dehalogenase/D4E1 pentamer fusion.

SEQ ID NO:45 is the DNA sequence encoding of the fusion protein of SEQ ID NO:44 (in *P. fluorescens* expression vector pMYC1803).

DETAILED DESCRIPTION OF PREFERRED EMBODIMENTS

The subject invention provides efficient and inexpensive methods of producing small peptides, including antimicrobial peptides (AMPs). According to the subject invention, bacteria (and other suitable microorganisms), preferably *Pseudomonas fluorescens* (*P. fluorescens*) in large-scale fermentations, are used to produce the peptides/AMPs. While AMPs are the preferred peptide for production according to the subject invention, components of the subject invention, alone or in combination, can be used or adapted for use to produce other types of peptides having therapeutic or catalytic utility.

Elements of the subject invention, alone and/or in combination, enable the surprisingly advantageous use of *P. fluorescens* to produce AMPs and other small peptides of interest. This invention broadly relates to the use of *P. fluorescens* to produce peptides, including AMPs. Thus, the subject invention includes a method for producing an antimicrobial peptide wherein said method comprises expressing a polynucleotide, preferably in a *P. fluorescens* cell, that encodes said peptide. Although producing AMPs in *P. fluorescens* is preferred, components of the subject invention, alone or in combination, can be used or adapted for use with other organisms and for producing peptides other than AMPs. This would be apparent to one skilled in the art having the benefit of this disclosure.

According to the subject invention, high levels of AMPs (or other small peptides) can be produced in bacteria (preferably *P. fluorescens*) as nontoxic concatemeric/multimeric precursors which are then cleaved to yield the active monomers. Producing AMPs in this manner tends to eliminate the toxicity of AMPs (which depends on their ability to assemble to form pores in bacterial membranes). Producing peptides, generally, in this manner can also help small peptides to avoid undesirable proteolytic degradation, to which small peptides are particularly susceptible.

One aspect of the subject invention is the multimers. Multimers of the subject invention can comprise two, three, four, five, or more peptide/AMP subunits. The exemplified constructs can be modified accordingly to produce the desired number of monomers in the multimer.

The subject invention provides efficient and inexpensive methods of producing small peptides, including antimicrobial peptides (AMPs). The expression systems according to the present invention have unexpectedly been found to provide transgenic polypeptide yields on the order of and in excess of 1 g/L, and often about 5 g/L. These yields represent a substantial improvement over those of the systems already reported in use in the industry.

In a particularly preferred embodiment, bacteria (and other suitable microorganisms), preferably *Pseudomonas fluorescens* (*P. fluorescens*) in large-scale fermentations, are used to produce the peptides. While AMPs are the preferred peptide for production according to the subject invention, and *P. fluorescens* is the preferred microbe, components of the subject invention, alone or in combination, can also be used or adapted to produce other types of peptides with other types of microbes.

As used herein, the term "peptide" indicates an oligopeptide or polypeptide molecule that contains at least two amino acids, in which molecule the amino acids thereof are attached one-to-another solely by peptide bonds. Peptides according to the present invention are any such oligopeptide or polypeptide molecules that are: functional peptides; structural peptides; fragments thereof; precursors thereof; combinations of any of the foregoing; and/or concatemers of any of the foregoing.

As noted above, peptides useful in the present invention include those that are: functional peptides; structural peptides; fragments thereof; precursors thereof; combinations of any of the foregoing; and/or concatemers of any of the foregoing.

Useful functional peptides include, but are not limited to, e.g.: bio-active peptides (i.e. peptides that exert, elicit, or otherwise result in the initiation, enhancement, prolongation, attenuation, termination, or prevention of a biological function or activity in or of a biological entity, e.g., an organism, cell, culture, tissue, organ, or organelle); catalytic peptides; microstructure- and nanostructure-active peptides (i.e. peptides that form part of engineered micro- or nano-structures in which, or in conjunction with which, they perform an activity, e.g., motion, energy transduction); and stimulant peptides (e.g., peptide flavorings, colorants, odorants, pheromones, attractants, deterrents, and repellants).

Useful bio-active peptides include, but are not limited to, e.g.: immunoactive peptides (e.g., antigenic peptides, allergenic peptides, peptide immunoregulators, peptide immunomodulators); signaling and signal transduction peptides (e.g., peptide hormones, cytokines, and neurotransmitters; receptors; agonist and antagonist peptides; polypeptide targeting and secretion signal peptides); and bio-inhibitory peptides (e.g., toxic, biocidal, or biostatic peptides, such as peptide toxins and antimicrobial peptides).

Useful structural peptides include, but are not limited to, e.g.: peptide aptamers; folding peptides (e.g., peptides promoting or inducing formation or retention of a physical conformation in another molecule); adhesion-promoting peptides (e.g., adhesive peptides, cell-adhesion-promoting peptides); interfacial peptides (e.g., peptide surfactants and emulsifiers); microstructure and nanostructure-architectural peptides (i.e. structural peptides that form part of engineered micro- or nano-structures); and pre-activation peptides (e.g., leader peptides of pre-, pro-, and pre-pro-proteins and -peptides; inteins).

This invention broadly relates to the use of *P. fluorescens* to produce AMPs and other small peptides. Elements of the subject invention, alone and/or in combination, enable the surprisingly advantageous use of *P. fluorescens* to produce small peptides, including AMPs. Various elements of this invention can also be used, alone or in combination, with other organisms (and for other purposes), as would be apparent to one skilled in the art having the benefit of this disclosure.

According to the subject invention, high levels of AMPs (and other small peptides) can be produced in bacteria (preferably *P. fluorescens*) as nontoxic concatemeric/multimeric precursors which are then cleaved to yield the active monomers. Producing AMPs in this manner tends to eliminate the toxicity of AMPs (which appears to depend on their ability to assemble to form pores in bacterial membranes). Producing peptides, generally, in this manner can also help small peptides to avoid undesirable proteolytic degradation, to which small peptides are very susceptible.

The subject invention provides multimers (preferably AMP multimers) and AMPs (and other peptides) having structural features that are unlike any previously taught or suggested in the art. The subject invention provides a novel means for linking AMP/peptide monomers to form multimers. The subject invention also provides a novel means for cleaving the monomers from the multimers. Preferred concatemeric precursors of the subject invention contain Asp-Pro peptide linkage/acid cleavage sites between the individual AMP/peptide subunits (monomers). Gly-Asp-Pro linkage is particularly preferred. This allows for inexpensive, efficient cleavage of the multimer to yield the active monomers. A dilute mineral or organic acid is the preferred cleavage agent. The use of such cleavage/cleavage sites between each copy of peptide/AMP monomers in a multimer was not taught in the art.

Also disclosed is a method for assembling multiple copies of peptide-encoding polynucleotides in preferred orientations in the multimeric construct while at the same time introducing acceptable cleavage sites. That is, in addition to having acceptable cleavage sites in the multimer, the subject invention provides DNA sequences that encode the cleavage sites wherein the corresponding DNA sequences allow for efficient and inexpensive assembly of multiple copies of the peptide/AMP "genes" in the desired orientations. Unlike other known gene construction methods, this aspect of the subject invention is compatible with providing specific chemical cleavage methods that generate minimally modified, active AMP/peptide products.

The subject invention also provides fusion proteins preferably comprising the subject concatemers/multimers fused to a carrier polypeptide/protein. Such fusions can further enhance recovery levels of the peptide/AMP of interest. In embodiments of the subject application where a carrier polypeptide is used, fusing the carrier polypeptide to the N-terminus of the multimer is preferred. However, multimers of the subject invention can be adapted for use in a variety of expression systems not limited to terminal fusions. The classes of carrier polypeptides of the subject invention are also unique.

Another very surprising aspect of the subject invention is that preferred cationic AMP multimers of the subject invention lack charge balancing. Furthermore, preferred fusion proteins of the subject invention (which preferably comprise an AMP multimer fused to a carrier polypeptide) also lack charge balancing. That is, AMPs are typically cationic/positively charged. The subject invention relates to the surprising discovery that it is not necessary to offset the positive charges of multiple copies of AMPs in multimeric constructs. The prior art taught against this, i.e., that a sufficient number of negatively charged amino acids had to be added in the carrier protein and/or to the multimer to completely offset (or at least to significantly neutralize) the net positive charge of the AMP(s). The subject invention thus eliminates this element that the art heretofore taught was required for microbial expression of multimeric AMP constructs. This aspect of the subject invention is also particularly advantageous for use with cationic peptides other than AMPs, as well.

Therefore, the subject invention enables the use of a broader range of carrier polypeptides than was previously envisioned. The subject invention surprisingly teaches that, instead of limiting carrier proteins to those that are anionic (i.e., about as anionic as the AMP is cationic), preferred carrier proteins or polypeptides should be selected because they are, themselves, expressed well in the host of interest.

The multimers and the multimeric fusion proteins of the subject invention are preferably produced as insoluble protein inclusions. The *P. fluorescens* of the subject invention are advantageously well-suited for producing multimers in these forms. When expressed in bacteria, preferred concatemeric precursors of the subject invention partition into insoluble, inactive protein inclusion bodies. After production, the dense inclusion bodies can be mechanically separated from the host cells. After solubilization with solvents or chaotropic agents, if desired, the concatemers can be cleaved using dilute acids to generate active AMP/peptide monomers. Alternatively and advantageously, weak acids are capable of both solubilizing the inclusions and cleaving the concatemers to the desired peptide product in one inexpensive step. The processes of the subject invention are capable of reducing costs relative to solid phase synthesis.

Thus, the subject invention provides a simple system for the economical production of peptides in microbes; the subject peptide expression systems can even be used to economically produce antimicrobial peptides. The *P. fluorescens* expression systems are preferred. While AMPs are preferred peptides, the expression systems of the subject invention can be used for the economical production of other kinds of peptides. In addition to avoiding the undesirable effects of intracellular proteases and having the capability of reducing the toxicity of AMPs, the subject acid-cleavage/carrier-concatemer system also makes expressing recombinant peptides more "process-friendly." That is, the peptides of interest can be separated from many host contaminants (other cellular components/remnants) by simple, inexpensive operations such as centrifugation or filtration. The desired fraction can then be easily converted to the active form by treatment with acid. The efficient coupling of the *P. fluorescens* fermentation system with the inexpensive processing procedure demonstrated herein provides a highly competitive process for the production and purification of naturally derived peptides.

The subject invention provides multimers and peptides (including AMPs) having structural features that are unlike any previously taught or suggested in the art. The subject invention provides a novel means for linking peptide/AMP monomers into multimers. Preferred concatemeric precursors of the subject invention contain Asp-Pro peptide bonds/cleavage sites between the individual (antimicrobial) peptide subunits (monomers). Gly-Asp-Pro linkage is particularly preferred. A dilute acid, either an organic or mineral acid, is the preferred cleavage agent, which allows for inexpensive, efficient cleavage of the multimer to yield the active monomers.

The use of such cleavage/cleavage sites between each copy of the (AMP) monomers was not taught in the art; one would typically expect extra amino acid residues to destroy or negatively impact the activity of the peptide/AMP. Thus, the use of acid-labile Asp-Pro linkages between the monomers yields, upon cleavage, derivitized AMPs that surprisingly retain their antimicrobial activity. The subject invention thus broadly relates to AMPs with such extensions (additional amino acid residues at the N- and C-termini), to AMP multimers having Asp-Pro cleavage sites (as well as Gly-Asp-Pro linkage) between the monomers, and to polynucleotides that encode these embodiments. The subject invention also relates generally to the use of dilute acids to cleave AMP monomers from an AMP multimer.

One surprising aspect of the subject invention is that the subject cleavage sites and the preferred dilute acid cleavage thereof yield active monomers that each include the core peptide/AMP together with additional amino acid residues at the N- and C-termini. Preferably, on each of the AMP monomers that result from acid cleavage of the multimers, there are approximately three additional amino acid residues-two residues at the C-terminus and one residue at the N-terminus. The exemplified monomers include the core AMP plus a proline residue at the amino terminus of the core AMP, and glycine and aspartic acid residues at the C terminus. It is surprising that such monomers retain excellent (antimicrobial) activity because the art heretofore taught that residual amino acids on the peptide/AMP, especially acidic/anionic residues on both termini of a core AMP/cationic peptide, would typically destroy the (antimicrobial) activity of the peptide (AMP). There was no reason to assume that this "extended" peptide would have been active; one would normally expect it to lack the desired activity. Thus, this aspect of the subject invention is particularly advantageous for the production of cationic peptides, preferably AMPs.

Another related aspect of the subject invention is the novel means for cleaving the monomers from the multimers. According to the subject invention, an organic acid, preferably a dilute acid such as 0.025 N HCL or 10% acetic acid, is preferably used as the cleavage agent for separating the active peptides/AMP monomers from the multimer (and from the carrier polypeptide if one is used). While there are a variety of cleavage agents that can be adapted for use according to the subject invention (various references discussed in the Background section, above, use a variety of cleavage agents), dilute acids of the subject invention are preferred for several reasons. One advantage is that the monomers resulting from the preferred dilute organic acid cleavage are natural products; some cleavage agents yield undesirable chemical derivatives that would not occur in nature. This is true for cyanogen bromide, for example. Formic acid can also yield residues that are undesirably formylated. Formic acid is also difficult to remove. (After cleavage of the multimer and extraction of the monomers using formic acid, the formic acid can be difficult to separate from the aqueous product because it forms a maximum-boiling azeotrope with water. This effect can cause the water to boil off faster than the formic acid, which lengthens the removal step of the formic acid.) Thus, a dilute acid other than formic acid is surprisingly preferred. This is contrary to prior teachings.

A desired peptide/antimicrobial peptide of the subject invention is preferably expressed by a cell initially as part of a multimeric precursor that comprises at least two peptide/AMP monomers. A preferred production method further includes the step of cleaving a multimeric AMP/peptide with a dilute acid to liberate the AMP/peptide monomers. In specifically exemplified embodiments, the AMP monomer resulting from said cleavage is the peptide represented by SEQ ID NO:7. In exemplified embodiments of the multimer, the multimer comprises the amino acid sequence of SEQ ID NO:6. A variety of other peptides and multimers are exemplified herein. A variety of additional peptide monomers, aside from the specifically exemplified AMP monomers, can be substituted. Constructs and polynucleotides that encode any of the peptides/proteins discussed, exemplified, and/or suggested herein are included in this invention.

In addition to having acceptable cleavage sites in the multimer, the corresponding DNA sequence that encodes the cleavage site must also allow for efficient and inexpensive assembly of multiple copies of the peptide/AMP "genes" in the desired orientations. Also disclosed is a method for assembling multiple copies of peptide/AMP-encoding polynucleotides in preferred orientations in the multimeric construct while at the same time introducing acceptable cleavage sites. The highly expressed carrier polypeptide of the carrier-AMP fusion polypeptide will be selected from any proteins or polypeptides that are highly expressed in the microbial host cell, examples of which include thoredoxin, maltose binding protein, and hydrolases excluding nitrilases. In a preferred embodiment using a hydrolase, a highly expressed glycosidase (EC 3.2.1.) or a highly expressed dehalogenase (EC 3.8.1.) will be selected. Preferred examples of highly expressed glycosidases are galactosidases, e.g., beta-galactosidases (EC 3.2.1.23). Preferred examples of highly expressed dehalogenases are haloalkane dehalogenases (EC 3.8.1.5), e.g., the haloalkane dehalogenase (SEQ ID NO:30) from *Rhodococcus rhodochrous* TDTM-003, an organism available as ATCC 55388 from The American Type Culture Collection (ATCC) (P.O. Box 1549, Manassas, Va. 20108 USA, located at 10801 University Blvd., Manassas, Va. 20110 USA).

Because the carrier polypeptide will be expressed as the initial, i.e. N-terminal, portion of the carrier-plus-peptide construct, the N-terminal portion of the construct may contain either the entire, selected, highly expressed protein or polypeptide or an N-terminal fragment thereof. Preferably, the N-terminal portion of the construct will be, i.e. will represent, an N-terminal fragment of the selected, highly expressed protein or polypeptide. Preferably, the N-terminal fragment will be at least 10 amino acid residues in length. In a preferred embodiment, the N-terminal fragment will be about or at least 15 amino acid residues in length. In a preferred embodiment, the N-terminal fragment will be about or at least 20 amino acid residues in length. In a preferred embodiment, the N-terminal fragment will be less than 150, more preferably about or less than 120, still more preferably about or less than 100, even more preferably about or less than 80, and yet more preferably about or less than 60 amino acid residues in length. In a preferred embodiment, the N-terminal fragment will be about 10 to about 150, more preferably about 10 to about 120, even more preferably about 15 to about 100, still more preferably about 15 to about 80, and yet more preferably about 20 to about 60 amino acid residues in length. In a preferred embodiment, the N-terminal fragment will be about 50 or about 40 or about 30 or about 20 amino acid residues in length. In a preferred embodiment, the carrier polypeptide will be selected from those that are not highly anionic, where highly anionic is defined as having a pKa or pI less than or equal to 5.5. Thus, preferably, the carrier polypeptide will have a pKa or pI greater than 5.5.

The amino acid sequence of the carrier polypeptide will be obtained or derived from the N-terminal amino acid sequence of the selected, highly expressed polypeptide. The initial selection of the carrier polypeptide with respect to charge balancing considerations is described with reference to four classes of amino acids. In a preferred embodiment, the amino acid sequence of the carrier polypeptide will be identical to that of the N-terminal portion of the selected, highly expressed polypeptide; in a preferred embodiment, it will be a conservative variant of the amino acid sequence of that N-terminal portion. As used herein, the phrase "conservative variant" refers to conservatively mutated versions of an amino acid sequence, here that of the selected carrier polypeptide. Conservative mutations of an amino acid sequence are defined as amino acid substitutions made within one or more of the following seven groups: Acidic: Asp, Glu; Uncharged Polar Amides: Asn, Gln; Basic: Lys, Arg, His; Small Uncharged or Non-Polar: Gly, Ala; Non-Polar Alkyl: Val, Leu, Ile; Polar Alcohol: Ser, Thr; Aromatic: Phe, Trp, Tyr. In a preferred embodiment of a conservative variant, less than 75% and more preferably less than 50% of the amino acid residues will be mutated; preferably up to or about 33%, more preferably up to or about 30%, even more preferably up to or about 25%, yet even more preferably up to or about 20%, still even more preferably up to or about 10%, and yet even more preferably up to or about 5% of the amino acid residues will be mutated. Where the amino acid sequence of the carrier polypeptide is either identical to or a conservative variant of that of the highly expressed polypeptide, its polynucleotide coding sequence may be codon-optimized for the host cell selected.

Although the examples below are described with reference to carrier polypeptides that are on the order of about 120 to 160 amino acids in length, carrier polypeptides have also been successfully used that are about 20 amino acids in length. For example, N-terminal 20-mer fragments of the *Rhodococcus rhodochrous* haloalkane dehalogenase have been used to express AMP concatemers with no reduction in expression of the carrier-plus-peptide fusion protein, as compared with the levels of expression observed for the larger carrier polypeptide constructs disclosed in the Examples.

The peptides according to the present invention are biosynthetically produced in a microbe, i.e. in a microbial host cell. As used herein, the terms "microbe" and "microbial" refer to fungi (including filamentous fungi and yeasts) and bacteria. Preferred filamentous fungi include species of, e.g., *Aspergillus*, *Chrysosporium*, *Neurospora*, and *Trichoderma*; preferred yeasts include species of, e.g., *Candida*, *Kluyveromyces*, *Pichia*, *Saccharomyces*, *Schizosaccharomyces*, *Yarrowia*, and *Zygosaccharomyces*. In a particularly preferred embodiment, the microbe will be a bacterium.

In a preferred embodiment in which a bacterium is selected as the microbial host cell, the bacterium will be a member of the phylum Firmicutes, more preferably a member of the class Bacilli. When a bacterium of the Bacilli is selected as host cell, preferably it will be a member of the order Bacillales or the order Lactobacillales. When a bacterium of the Bacillales is selected, preferably it will be a member of the family Bacillaceae, more preferably a member of the genus *Bacillus*, e.g, *Bacillus subtilis*; when a bacterium of the Lactobacillales is selected, preferably it will be a member of the family Lactobacillaceae, more preferably a member of the genus *Lactobacillus*. In an alternative preferred embodiment in which a bacterium is used as the host cell, the bacterium will be a member of the phylum Actinobacteria, preferred examples of which include species of the genus *Corynebacterium*, the genus *Rhodococcus*, and the genus *Streptomyces*.

In a particularly preferred embodiment using a bacterial host cell, the bacterium will be a member of the phylum Proteobacteria, more preferably a member of the gamma Proteobacteria. When a bacterium of the gamma Proteobacteria is selected as the host cell, preferably it will be a member of the order Enterobacteriales or the order Pseudomonadales. When a bacterium of the Enterobacteriales is selected, preferably it will be a member of the family Enterobacteria, more preferably a member of the genus *Escherichia* or the genus *Serratia*. A preferred example of an *Escherichia* species is *E. coli*; a preferred example of a *Serratia* species is *S. marcescens*.

When a bacterium of the Pseudomonadales is selected, preferably it will be a member of the family Pseudomonadaceae, and still more preferably a member of the genus *Pseudomonas*. Where a *Pseudomonas* bacterium is selected as host cell, preferably it will be a member of the *P. chlororaphis*-*P. fluorescens* group, which contains: the *Pseudomonas chlororaphis* group, e.g., *P. aurantiaca*, *P. chlororaphis*, *P. fragi*, *P. lundensis*, and *P. taetrolens*; and the *Pseudomonas fluorescens* group, e.g., *P. azotoformans*, *P. brenneri*, *P. cedrina*, *P. congelans*, *P. corrugata*, *P. costantinii*, *P. extremorientalis*, *P. fluorescens*, *P. fulgida*, *P. gessardii*, *P. libanensis*, *P. mandelii*, *P. marginalis*, *P. mediterranea*, *P. migulae*, *P. mucidolens*, *P. orientalis*, *P. poae*, *P. rhodesiae*, *P. synxantha*, *P. tolaasii*, *P. trivialis*, and *P. veronii*.

More preferably, the bacterial host cell will be a member of the *Pseudomonas fluorescens* group, preferably *P. fluorescens*. When *P. fluorescens* is selected, preferably it will be one of *P. fluorescens* biovar A, *P. fluorescens* biovar B, *P. fluorescens* biovar C, *P. fluorescens* biovar G, *P. fluorescens* Pf-5, *P. fluorescens* Pf0-1, or *P. fluorescens* SBW25. *P. fluorescens* biovar A is particularly preferred.

The small peptides produced according to the present invention will be at least 2 amino acids in length. Preferably, the small peptides will be about or at least 5, more preferably about or at least 10, still more preferably about or at least 15, even more preferably about or at least 20, and yet more preferably about or at least 25 amino acids in length. Preferably, the small peptides will be about or less than 300, more preferably about or less than 250, even more preferably about or less than 200, yet more preferably about or less than 180, still more preferably about or less than 150, and yet even more preferably about or less than 120 amino acids in length. Where the small peptides are less than 120 amino acids in length, preferably they will be about or less than 100, more preferably about or less than 80, even more preferably about or less than 60, still more preferably about or less than 50, yet more preferably about or less than 40, and yet even more preferably about or less than 30 amino acids in length.

In a preferred embodiment, the small peptides will be 2 to about 100, more preferably about 5 to about 80, still more preferably about 5 to about 60, even more preferably about 5 to about 50, still more preferably about 10 to about 40, even more preferably about 15 to about 40, and yet more preferably about 20 to about 30 amino acids in length.

In an alternative preferred embodiment, the small peptides will be about 5 to about 300, more preferably about 10 to about 250, even more preferably about 15 to about 200, yet more preferably about 20 to about 180, still more preferably about 25 to about 150, and yet even more preferably about 30 to about 120 amino acids in length. The amino acid sequence of the small peptide may be identical to, and obtained from, that of a peptide native to a biological organism; or the sequence may be synthetic, i.e. it may be a result of human intervention, as by application of a genetic engineering technique or process, whether stochastic or rational. In a preferred embodiment, where the amino acid sequence of the small peptide is obtained from a biological organism, preferably the organism will be a mesophilic organism.

In a preferred embodiment, the small peptides produced according to the process can be further treated to remove terminal amino acid residues contributed by the cleavage site peptide(s), the cleavable linker peptide(s), or both. This may be performed by enzymatic or chemical means such as are known in the art.

As described herein, the transgene used in the present invention will contain a carrier polypeptide expressed upstream of (i.e. in the N-terminal position relative to) a peptide multimer construct, i.e. a concatemer of peptides. The term "multimer," as used herein in regard to peptide multimers, indicates a polypeptide that contains two, three, or more peptide units. Thus, the peptide multimer will be at least a dimer. In a preferred embodiment, the peptide multimer will be at least a trimer. The peptide multimer construct will include, not only at least two small peptides (the peptide units), but at least one peptidyl cleavage site between and connecting the peptides in tandem. In a preferred embodiment, the peptide multimer will be about or less than 600 amino acids in length. Preferably, the peptide multimer will be about or less than 500, more preferably about or less than 450, even more preferably about or less than 400, yet more preferably about or less than 350, still more preferably about or less than 300, yet even more preferably about or less than 250, still even more preferably about or less than 200, even further preferably about or less than 150 amino acids in length. Preferably, the peptide multimer will be about or at least 10, more preferably about or at least 15, even more preferably about or at least 20, still more preferably about or at least 25, yet more preferably about or at least 30, still even more preferably about or at least 40, yet even more preferably about or at least 50, further preferably about or at least 60, even further preferably about or at least 70, yet further preferably about or at least 80, still further preferably about or at least 90, and yet even further preferably about or at least 100 amino acids in length. In a preferred embodiment, the peptide multimer will be about 10 to about 600, more preferably about 15 to about 500, even more preferably about 20 to about 450, yet more preferably about 25 to about 400, and still more preferably about 30 to about 300 amino acids in length.

In summary, the results presented herein show that the unique concatemeric peptide/AMP constructs of the subject invention can be efficiently produced in microbes, more preferably bacteria, and most preferably *P. fluorescens*. Concatemerization of AMP genes seems to have two noticeable effects on the antimicrobial peptide: it reduces toxicity (both extra- and intra-cellular), and it may increase intracellular partitioning and inclusion body formation, thereby reducing susceptibility to proteases, and further mitigating toxic effects.

While concatemerization of peptide/AMP genes was found to be sufficient to facilitate adequate expression of the desired peptide, a carrier polypeptide (a dehalogenase is one example) was used to create even higher expression levels of the peptide/AMP. The use of a multimer/concatemer together with a carrier polypeptide is preferred, especially in *P. fluorescens*, to promote very high expression.

The subject invention also provides fusion proteins preferably comprising the subject concatemers/multimers fused to a carrier polypeptide/protein. Such fusions can further enhance recovery levels of the peptide of interest. A truncated form of a full-length protein (one example is the N-terminal 123 residues of the dehalogenase) can also work as well as (or better than) a full-length protein as an enabling fusion partner. Such truncated proteins may not be fully folded and can be less soluble than the full-length protein. These fusion proteins may also partition to the insoluble lysate fraction. This type of an incapacitated protein fragment may thus readily aggregate and precipitate, advantageously pulling the tethered peptide/AMP concatemer out of solution where it would otherwise have been readily exposed to proteases.

Both gene concatemerization and the use of certain fusions are advantageous for the construction of non-toxic, highly expressed peptide/AMP constructs. While the formation of inclusion bodies may facilitate accumulation of expressed peptides, this does not appear to be the only reason that high expression levels were presently achieved. For example, a DHFR (dihydrofolate reductase)-AMP (monomeric) fusion was observed to strongly partition to form inclusion bodies; however, this construct was still toxic to the *P. fluorescens* host. SDS-PAGE analysis of these DHFR-AMP inclusion bodies suggested that the AMP peptide was cleaved from the DHFR fusion protein. This proteolysis may have exposed the cells to the liberated (and toxic) AMP. Concatemerization of the AMP molecules, especially when fused to a carrier polypeptide (such as DHFR or dehalogenase), provides an additional level of protection to the cell in the event of such proteolysis.

In embodiments of the subject application where a carrier polypeptide is used, fusing the carrier polypeptide to the N-terminus of the multimer is preferred. However, multimers of the subject invention can be adapted for use in a variety of expression systems not limited to terminal fusions. The subject carrier polypeptides can also be used in a variety of ways not specifically exemplified herein (with monomers as opposed multimers, for example).

The critical parameters identified herein enable a wide range of "next-generation" expression constructs for improved peptide/AMP expression. Coupling highly expressed constructs with the attractive, low-cost attributes of *P. fluorescens* fermentation will now enable the economical production of peptides/AMPs for novel, high-volume applications. The processes exemplified herein can be implemented in high density fermentations. Preferably, *Pseudomonas fluorescens* is the bacteria used in these large scale fermentations. The subject invention enables greatly improved yields of the peptide/AMP as compared to those heretofore known in the art.

Another very surprising aspect of the subject invention is that cationic AMP multimers can lack charge balancing. Furthermore, the fusions of the subject invention (which comprise a multimer fused to a carrier polypeptide/protein) can also lack charge balancing. That is, AMPs are frequently cationic/positively charged. The subject invention relates to the surprising discovery that it is not necessary to offset the positive charges of multiple copies of AMPs in multimeric constructs. Multimers and fusions of the subject invention advantageously but surprisingly do not require the balancing of charges in the multimer or in the complete fusion. The subject invention eliminates an element that the art heretofore taught was required in multimeric AMP constructs. Some prior attempts were made in the art to biologically produce AMPs by first producing inactive AMPs in the form of multimeric and/or fusion proteins; however, it was heretofore thought that a sufficient number of negatively charged amino acids had to be added by way of the carrier protein or to the multimer to completely offset the positive charge of the AMP(s). Some type of an acidic protein was required (in the multimer and/or in the carrier) to balance out the basic (pH) nature of the AMPs. The art heretofore taught that, during translation, the nascent AMP or AMP multimer (which are cationic/positively charged/basic) would interact with nucleic acid molecules involved in translation, and that this would effectively stop translation. Thus, carrier proteins were heretofore selected for having anionicity sufficient to balance or negate the charge of the AMP. As will be apparent in light of this disclosure, the subject invention is also particularly advantageous for producing cationic peptides other than AMPs.

The subject invention surprisingly and advantageously provides carrier polypeptides that are preferably either cationic or not sufficiently anionic to significantly offset the positive charge of the AMP/AMP multimers. In other words, the net positive charge of the multimeric AMPs and AMP fusions are not significantly offset and/or balanced by acidic/negatively charged amino acid residues. The subject invention surprisingly and advantageously departs from what was heretofore taught in the art; offsetting, negatively charged amino acid segments are absent from the multimers and from the fusions of the subject invention. Likewise, the subject polynucleotides are free of a component that is ultimately responsible for significantly reducing the cumulative positive charge of the encoded AMPs. Furthermore, the spacers and the carrier polypeptide of the subject invention (as well as the AMP subunits) do not have added cysteine residues, contrary to what some of the prior art suggested.

The following table (Table 2) illustrates that for the present purposes, there are four classes of amino acids: two of the classes (nonpolar and uncharged polar) are for uncharged amino acids, and the other two classes (acidic and basic) are for amino acids that contribute a charge to the protein/peptide of which they are a part. As used herein, "acidic" amino acids add negative charges to a protein, and "basic" amino acids add positive charges to a protein.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject discovery that charge balancing is not essential provides a much greater range of multimers and carrier polypeptides available for use according to the subject invention. Thus, the subject invention enables the use of a broader range of multimers and carrier polypeptides than the art previously envisioned. The subject invention provides cationic multimers. The classes of carrier polypeptides of the subject invention are also unique. The subject invention surprisingly shows that rather than limiting the carrier proteins to those that are sufficiently anionic (about as anionic as the AMP multimer is cationic), the subject invention teaches that preferred carriers are proteins or polypeptide fragments that are themselves expressed well in the host of interest. This expression level is preferentially from 2 to 25% of the total cellular protein. The subject invention also provides carrier polypeptides that tend to be insoluble so that they drive the fusion proteins out of solution in the cytoplasm and into insoluble inclusion bodies/protein aggregates. Carrier polypeptides of the subject invention advantageously precipitate out the attached peptides/AMPs; this may help to improve recovery levels of the peptide/AMP by decreasing the susceptibility of an otherwise soluble peptide/AMP to cytoplasmic proteases, and reduce intracellular activity of toxic peptides eg., AMPs.

The multimeric fusion proteins of the subject invention are preferably produced as insoluble protein inclusions. The *P. fluorescens* of the subject invention are advantageously well-suited for producing multimeric AMPs in this form.

As implied above, the subject invention includes polynucleotide constructs wherein each such construct comprises a DNA segment that encodes a segment of amino acids as discussed or suggested herein. Preferably, the DNA segment that encodes a multimer and/or a fusion protein of the subject invention is "operably linked," or placed into a functional relationship with another nucleotide sequence, so that the DNA segment can be expressed (transcribed and translated) in cells of interest in order to produce the protein(s) of interest. For instance, a promoter that is functional in *P. fluorescens* can be operably linked to a coding sequence so that the promoter effects the transcription of the coding sequence. Generally, "operably linked" means that the sequences being linked are contiguous and, where necessary to join two protein coding regions, contiguous and in frame. However, it is well known that certain genetic elements, such as enhancers, can be operably linked even if they are not contiguous.

DNA constructs prepared for introduction into a prokaryotic or eukaryotic host (i.e., vectors) will typically comprise a replication system recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included to promote secretion of the polypeptides or to otherwise allow the protein to cross or bind cell membranes.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typically selection genes encode proteins that (a) confer resistance to antibiotics or other toxic substances, e.g., ampicillin, neomycin, methotrexate, etc.; (b) complement auxotrophic deficiencies; or (c) supply critical nutrients not available from defined growth media. The choice of the proper selectable marker will depend on the host cell; appropriate markers for different hosts are known in the art.

Transformants can also be detected by using hybridization probes comprising a nucleic acid sequence of interest. Preferably, hybridization is conducted under conditions of low, moderate, and/or high stringency as described in, for example, Keller, G. H., M. M. Manak (1987), *DNA Probes*, Stockton Press, New York, N.Y., pp. 169-170. Polynucleotides within the scope of the subject invention can be detected in this manner.

As used herein, a "recombinant" polynucleotide refers to a polynucleotide that is made by the combination of two otherwise separated segments of nucleic acid sequence, wherein the sequences are joined by artificial manipulation (by genetic engineering techniques or by chemical synthesis). In so doing, one can join together heterologous polynucleotide segments, with each having a desired function, to generate a polynucleotide having a desired combination of functions. As used herein, reference to "isolated" polynucleotides and/or "purified" proteins refers to these molecules when they are not associated with the other molecules with which they would be found in nature. Thus, reference to "isolated" and/or "purified" signifies the involvement of the "hand of man" as described herein.

Multimers, fusion proteins, and/or AMPs produced by said microbial cells according to the subject invention are preferably produced in an amount that is about 2% to 25% of the total cell protein produced by said microbial cell. These microbial cells are preferably grown (allowed to reproduce) to produce a large-scale batch culture of said microbial cells, and the multimers, fusion proteins, and/or AMPs are preferably produced as 2% to 25% of the total cell protein produced by the batch culture.

Likewise, an aspect of the subject invention is the microbial cells comprising a polynucleotide and/or a protein of the subject invention. Transgenic host cells, in the present context, are those which have been genetically modified to contain an isolated DNA molecule of the instant invention. The DNA can be introduced by any means known to the art which is appropriate for the particular type of cell, including without limitations, transformation, lipofection, electroporation, and physical bombardment. Transgenic cells also include the "natural" progeny of such artificially "transformed" cells which have the heterologous DNA of interest. The heterologous DNA is preferably incorporated in the genome of the host cell; techniques for accomplishing this are well known in the art. The polynucleotide of interest can also be strictly maintained and expressed in progeny cells by way of a non-genomic plasmid; techniques for accomplishing this are also well known in the art.

It is recognized by those skilled in the art that the DNA sequences may vary due to the degeneracy of the genetic code and codon usage. All DNA sequences which code for peptides and proteins discussed and exemplified herein are included in this invention.

Additionally, it will be recognized by those skilled in the art that allelic variations may occur in the exemplified polynucleotides and proteins/peptides which will not significantly change the desired activity of the proteins/peptides. All such equivalents are included within the scope of this invention. Conservative amino acid substitution can be made with respect to the classes of amino acids listed above in Table 1. In some cases, non-conservative changes can be made without significantly changing the desired activity/function of the proteins/peptides discussed herein.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Design and Production of Multimeric AMPs

The D2A21 antimicrobial peptide was used as an exemplary AMP with the subject production strategies. This core AMP is a 23-residue peptide of phenylanine, alanine, and lysine in an alpha-helical configuration:

```
                                              (SEQ ID NO:1)
Phe Ala Lys Lys Phe Ala Lys Lys Phe Lys Lys Phe
Ala Lys Lys Phe Ala Lys Phe Ala Phe Ala Phe
```

A gene that encodes this AMP was synthesized, and then a plasmid construct was built to express the D2A21 precursor in bacteria. First, a DNA sequence that encodes the D2A21 peptide was chemically synthesized. SEQ ID NO:2 shows the DNA sequence used to encode the D2A21 peptide of SEQ ID NO:1. This DNA molecule and its non-coding complement were ligated (in the correct orientation) to form multimers/concatemers. Acid-labile Asp-Pro cleavage sites were needed between each AMP monomer (that would be ligated to form a multimer) to allow for cleavage of the multimer to active monomers. Thus, the "core AMP" was modified to provide for linkers/cleavage sites for post-synthesis acid hydrolysis of the multimeric product (into functional monomers). In one example, nine additional DNA residues (bases) were added to the ends of the core D2A21 DNA sequence to add a flanking aspartic acid-proline sequence at the amino end of the D2A21 peptide and a glycine at the C-terminus. See SEQ ID NO:4, below. SEQ ID NO:3 is the DNA sequence used to encode SEQ ID NO:4. A glycine residue was added on the N-terminus of the Asp-Pro sequence to reduce any potential "neighboring group" effects on the cleavage reaction. The amino acid sequence of the core AMP plus the three additional amino acid residues is:

```
                                              (SEQ ID NO:4)
Asp Pro Phe Ala Lys Lys Phe Ala Lys Lys Phe Lys
Lys Phe Ala Lys Lys Phe Ala Lys Phe Ala Phe Ala
Phe Gly
```

Multiple copies of these subunits can then be joined to each other. Weak acids can then be used to cleave, in the flanking sequence, between the aspartic acid and proline residues.

Following (SEQ ID NO:6) is an exemplary dimer ("the 4A dimer") having two D2A21 antimicrobial peptides connected by the Gly-Asp/Pro cleavage sequence (two copies of SEQ ID NO:3 joined together) and flanked by short sequences of unrelated peptide. (For example, the six histidine residues as shown below were incorporated on the C-terminus of the multimer to allow for affinity purification of the multimers on immobilized Ni. See, e.g., Example 5, below.) The DNA sequence that was used to encode the following multimer is provided in SEQ ID NO:5.

```
                                              (SEQ ID NO:6)
Met Ala Ser Met Thr Gly Gly Gln Gln Met            10

Gly Arg Asp Pro Phe Ala Lys Lys Phe Ala            20

Lys Lys Phe Lys Lys Phe Ala Lys Lys Phe            30

Ala Lys Phe Ala Phe Ala Phe Gly Asp Pro            40

Phe Ala Lys Lys Phe Ala Lys Lys Phe Lys            50

Lys Phe Ala Lys Lys Phe Ala Lys Phe Ala            60

Phe Ala Phe Gly Asp Pro Asn Ser Ser Ser            70

Val Asp Lys Leu Ala Ala Ala Leu Glu His            80

His His His His His                                85
```

Asp-Pro acid cleavage sites can be noted between residues 13 & 14, 39 & 40, and 65 & 66. Thus, acid treatment of the above multimer yielded two AMP monomers (amino acids 14-39 and 40-65), each being called D2A21'. The sequence of the resulting D2A21' monomer is as follows:

```
                                              (SEQ ID NO:7)
Pro Phe Ala Lys Lys Phe Ala Lys Lys Phe Lys Lys
Phe Ala Lys Lys Phe Ala Lys Phe Ala Phe Ala Phe
Gly Asp
```

As compared to the D2A21 core peptide of SEQ ID NO:1, D2A21' contains an additional proline on the N-terminus and a glycine-aspartate dipeptide on its C-terminus. D2A21' was surprisingly found to possess equivalent antimicrobial activity as compared to the D2A21 core/parent peptide.

With aspartic acid and glutamic acid being acidic (negatively charged) amino acid residues, and lysine, arginine, and histidine being basic (positively charged) amino acid residues, the following arrangement of charged amino acids in the multimer of SEQ ID NO:6 is apparent:
  a single arginine (positively charged; residue 12 in SEQ ID NO:6) and a single aspartic acid (negatively charged; residue 13 in SEQ ID NO:6) in the leader sequence (the first 13 amino acids in SEQ ID NO:6),
  9 lysines (positively charged) in the first D2A21 subunit (amino acids 14-39 of SEQ ID NO:6), which ends with a single aspartic acid (negatively charged; residue 39),
  9 lysines in the second D2A21 peptide (amino acids 40-65) which ends with a single aspartic acid (residue 65), and
  1 aspartic acid and 1 glutamic acid (each negatively charged) and 6 histidines (positively charged) in the trailer sequence (amino acids 65-85).

The charges of the 85 amino acid residues of SEQ ID NO:6 can be illustrated as follows, where "O" represents a neutral amino acid residue, "+" represents a positively charged/basic amino acid residue, and "–" represents an acidic/negatively charged residue:
  OOOOOOOOOOO+– (13 amino acids in leader segment)
  OOO++OO++O++OO++OO+OOOOOO– (26-amino-acid D2A21')
  OOO++OO++O++OO++OO+OOOOOO– (D2A21')
  OOOOOO–OOOOOO–++++++ (20 amino acids in trailer segment)

Thus, it can be clearly seen that there are 25 positively charged residues and only 5 negatively charged residues in the multimer of SEQ ID NO:6. The positive charge resulting from the 18 lysine residues in the two AMPs (9 lysines in each one) would not be offset by the 3 aspartic acids of the leader and linker sequences and the single glutamic and aspartic acid residues of the trailer. It is additionally surprising that the leader sequence comprises a positively charged residue (arginine) and that the trailer sequence comprises 6 histidines, which are positively charged. The art heretofore taught against the use of multimers having additional, non-critical amino acids that have a positive charge. It is still further surprising that the three additional residues of D2A21', one of which is acidic, did not adversely affect the activity of D2A21' as compared to the core D2A21 peptide.

EXAMPLE 2

Synthesis of Constructs with Multiple-Copy, Correctly-Oriented AMP Units

Production costs for peptide products reside in the cost of both peptide synthesis and peptide purification. Large-scale chemical synthesis of peptide polymers is both time and labor intensive; for solid-phase peptide synthesis, thirteen to eighteen steps requiring a total of two to nineteen hours to complete are needed to add each residue to the polymer during synthesis (Mergler & Durieux, 2000). Furthermore, many of these steps may not go to completion or are prone to side-reactions, which results in the accumulation of numerous, varied side-products in the reaction mixture (especially for longer peptides). Consequently, the cost of synthesis can be very high (approaching $1,000,000 per kg), and the cost of purification can equal or exceed this amount, depending on the required level of purity. Clearly, such costs often greatly exceed the acceptable cost limits for large volume applications.

AMPs are usually comprised of periodically arranged hydrophobic and positively charged (basic) side chains (for recent reviews see Hancock and Lehrer, 1998, or Blondelle et al., 1999). AMPs are amphipathic molecules; the periodic arrangement of the residues imparts a spatial segregation of hydrophobic and charged side chains when the peptide adopts a structured (helical or β-sheet) conformation. This segregation of charge and hydrophobicity allows AMPs to bind to the outer membranes of microbes. Once bound, the peptides can insert into the membrane lipid bilayer and self-assemble into lytic pores (Hancock et al., 1995), which allow the contents of the cell to escape, causing microbial death in minutes. It has been proposed that AMP molecules kill microbes by inserting into microbial membranes and then assembling into pores that destroy the structural integrity of the membrane. Although the detailed mechanism of action is not totally understood, the predictable structural characteristics of these peptides make it possible to design active AMP molecules de novo.

In an attempt to inhibit the oligomerization/assembly process and in an attempt to decrease product solubility, we presently designed and created an expression construct in which the AMP product was expressed as "head-to-tail" linked polymers (concatemers). Such AMP concatemers were designed to reduce the solubility and the steric/structural plasticity of the AMP that is required for them to insert into the membrane and kill the microbial host cells. The insoluble concatemer polypeptide accumulated within the cell as insoluble inclusion bodies. After production, the concatemer could be harvested by lysing the cells and washing away the soluble host-related impurities.

All genes possess a 5' to 3' polarity which defines proper ("sense") expression. Ligation of identical DNA molecules into a concatemeric gene requires that all the subunits be ligated in a "head-to-tail" orientation (with respect to the 5' to 3' polarity of the DNA molecule). Each incorrectly oriented subunit not only is incorrectly produced ("antisense" expression) but also destroys proper expression of adjacent subunits. As the number of subunits in the concatemer increases, the probability of all randomly ligated subunits possessing the correct orientation becomes vanishingly small. In many instances, proper orientation during ligation can be efficiently accomplished using "forced" cloning techniques employing either two distinct restriction endonucleases or a class IIS endonuclease (Lee, J. H., et al., 1996, Kim & Szybalski, 1988). However, these conventional strategies are not useful for production of minimally modified cleavable peptide concatemers, as they would add a relatively large number of amino acids to the ends of the peptide (which heretofore would have been expected to diminish its activity). The subject ligation strategy allows for DNA termini that encode short cleavable amino acid sequences.

Figure 2:
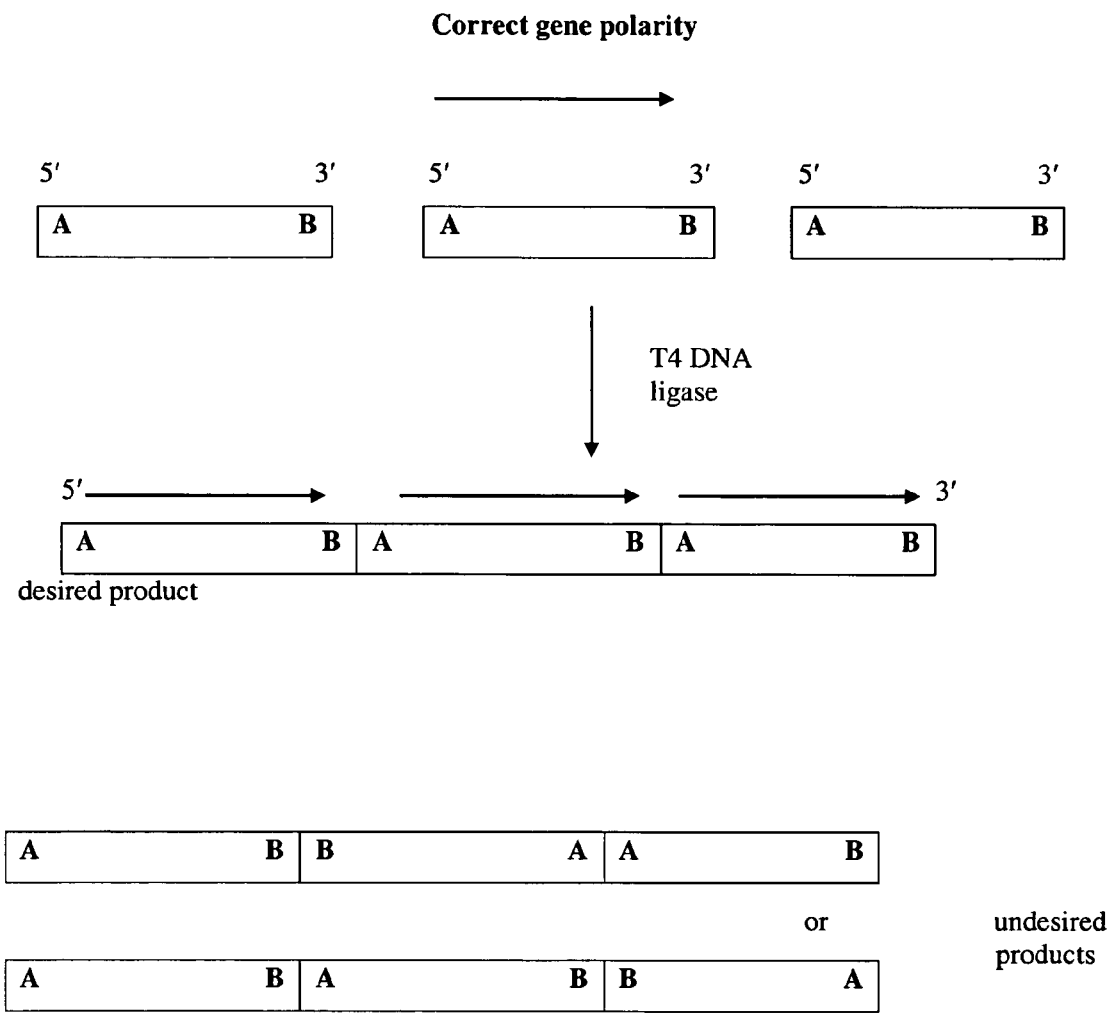
FIG. 2 shows an assembly of multimeric subunits in a desired orientation.

The subject invention also discloses, and advantageously utilizes, a method of concatemer construction that uses "pseudopalindromic spacers" to link the AMP subunits. This selective method allows the production of concatemers with correctly oriented subunits, i.e., in a head-to-tail arrangement (in order to eliminate clones having impractical arrangements). See FIGS. 1, 2, and 3A-3C. The synthetic DNA that encodes the AMP monomer contains an additional discontinuous sequence that forms a palindromic hexanucleotide endonuclease cleavage site only when incorrect termini are ligated. After (or during) ligation of the DNA subunits, incorrectly assembled concatemers can be conveniently degraded by digestion of the DNA with the appropriate endonucleases. As shown in FIGS. 2 and 3, PvuI recognizes the undesired B-B polarity, and BamHI recognizes the undesired A-A polarity.

These concatemers were created though oligonucleotide fusions using an antipolar, self-complementary DNA sequence overlap based on the "pseudopalindromic" sequence: 5'GATCCG3'. This sequence forms the core of one of the possible coding sequences making up the acid labile cleavage site used at the junctions of the AMP monomeric units, Gly-Asp-Pro. The sequences specifically used to accomplish this are shown in FIGS. 3A through 3C. Because these sequence ends are self complimentary they may ligate to themselves or to each other. In this case if they ligate to themselves the ligation will form either a PvuI or a BamHI restriction endonuclease site at the junction. If they ligate to each other, no restriction site will be formed. This latter case also creates contatameric products of the desired polarity. In fact any ligation between two self-complementary oligonucleotides which results in endonuclease cleavage site(s) being formed by the ligation for two of the three possible ligation products but not the third would be generically useful to assemble products containing desired polarity. Preferentially that the desired product of the ligation will not contain a formed endonuclease cleavage site(s) at the point of ligation.

After completion of the ligation and digestion process, the surviving concatemers should be correctly assembled (uniform sense orientation). Next, the concatemers of desired size can be purified and inserted into the expression plasmid. If an appropriate hexanucleotide sequence is chosen (GATCCG (SEQ ID NO:8)), it will encode a cleavable peptide linker connecting the AMP subunits, e.g., the Asp-Pro cleavable dipeptide linker.

Using this method, D2A21' concatemers were synthesized and inserted into the E. coli expression plasmid pET21b at the BamHI site in the multiple cloning site region. After transformation into E. coli, two clones were obtained, clones 4A and AB4, containing two and three D2A21' monomers respectively. The sequences for the 4A dimer are provided above. The AB4 trimer and the DNA used to encode it are provided in SEQ ID NOs:9 and 10, respectively. Although larger D2A21' concatemers (6, 7, and 8 subunits per concatemer) were purified and ligated into the expression plasmid, we focused further exemplary work on the use of these dimers and trimers.

EXAMPLE 3

Expression of AMP Concatemer Polypeptides in E. coli

The 4A dimeric and AB4 trimeric plasmids were transformed into E. coli strain BL21 (DE3). Transformant clones (antibiotic resistant colonies) were used to inoculate liquid growth medium. The resulting cultures were shaken at 37° C. When the culture density reached an A600 of 1, gene induction was performed by adding IPTG (isopropyl thiogalactoside) to the culture to a final concentration of 1 mM, and the cultures were incubated at 37° C. for three hours. After induction the cells were harvested, lysed, and centrifuged to separate the soluble/cytoplasmic and insoluble cellular components. These extracts were analyzed by SDS-PAGE. Prominent induced protein bands were observed in the samples from induced cultures expressing the dimeric (4A) or the trimeric (AB4) D2A21' constructs. As expected, these bands are not observed in SDS-PAGE analysis of samples from cultures that did not contain the AMP gene.

The D2A21' peptide is very rich in the amino acids lysine, phenylalanine, and alanine. To determine whether D2A21' concatemer production levels could be increased by adding additional amino acids to the growth medium, we added 0.5 g/l each of phenylalanine and lysine to the cultures immediately after induction. This supplementation step appeared to significantly improve the production levels of the D2A21' dimer in E. coli.

EXAMPLE 4

Purification and Partitioning of AB4 from E. coli

The plasmid encoding the AB4 gene was transformed into the E. coli expression host BL21(DE3) and the resulting antibiotic resistant colonies were used to inoculate flasks containing rich induction medium. The resulting cultures were grown at 37° C. to an A600 nm of 1 and induced with 1 mM IPTG for three hours at 37° C. After induction the culture was harvested by centrifugation, lysed and centrifuged to separate the soluble cellular components (such as the cytoplasm) from the insoluble cellular components (like the cell membranes or proteinaceous inclusion bodies). The AB4 D2A21' trimer is well expressed in E. coli and partitions to the insoluble subcellular fraction.

To determine whether the AB4 protein forms inclusion bodies or is associated with cell membranes, the insoluble fraction was washed with buffer detergent solution. The AB4 protein could not be extracted with 1% TRITON™ X-100, a nondenaturing detergent. This detergent solution would be expected to solubilize membrane lipids and proteins. Anionic detergents such as SDS solubilize the AB4 protein very well. This result is not surprising since strong favorable interactions might be expected between anionic detergents and the cationic peptides. Conversely, the AB4 trimer is not solubilized by cationic detergents. Cationic detergents may be useful in the selective solubilization of host-related impurities from the AB4 protein.

The observation that the AB4 protein cannot be solubilized by nonionic detergents such as TRITON™ X-100 suggests that the protein is not bound to membranes. Rather, our collective data suggests that the AB4 protein forms inclusion bodies within the cell. This is also advantageous from a process-development perspective because inclusion-body products can be purified from many contaminants using inexpensive physical techniques such as centrifugation or filtration.

EXAMPLE 5

Purification of Soluble Polypeptide

In order to characterize the bacterially expressed concatemers, the 4A (D2A21) dimer was purified using immobilized Ni++ chromatography. The majority of the dimer partitions to the soluble cytoplasmic fraction, unlike the trimer discussed in Example 4, which partitions to the insoluble fraction. E. coli lysates from cells expressing the 4A dimeric D2A21' concatemer were prepared and passed over an immobilized Ni column. After washing the column with buffer to remove unbound material, the concatemer was specifically eluted using 0.5 M imidazole, pH 7.8. The Ni++-purified dimer appears as a single band possessing an apparent MW of about 13 kDa; the apparent high molecular weight of the purified dimer may result from the highly cationic nature of this polypeptide. The product yield from the Ni-column was lower than expected, possibly due to tight, nonspecific interactions between the amphipathic peptide and the solid support or because of poor binding of the multimer to the support. The purified protein was dialyzed to remove the imidazole prior to functional and biochemical analysis.

MALDI mass spectrometry analysis of the purified dimer indicates that the N-terminal methionine is removed (expected MW=9,497.1; observed MW of purified dimer=9,499.4). This modification is commonly observed for this protein expression system. Using the protocol discussed below in Example 7, it was determined that the dialyzed D2A21 dimer possessed no detectable antimicrobial activity. This showed that antimicrobial activity of the peptide was attenuated through concatemerization.

EXAMPLE 6

Generation of Peptide Monomers from Multimers

To determine whether D2A21' could be obtained from exemplified concatemers, the purified (inactive) precursor was treated with 50% formic acid (or water as a control) and the mixture was heated to 70° C. for 24 hours. After the cleavage period, the samples were vacuum dried using a speed vac and the samples were neutralized with TrisCl/NaOH prior to analysis. The samples were analyzed by SDS PAGE analysis. The analysis indicated that, as expected, the precursor polypeptide was cleaved by formic acid (but not by water). A discrete ladder of these cleavage intermediates plus uncleaved material was observed at an earlier time point (6 hours) for the formic acid treated samples. Other acid treatments are discussed elsewhere herein; the key to cleaving the peptides is lowering the pH (which one skilled in the art would recognize in light of the subject disclosure).

EXAMPLE 7

Activity of the Monomers Obtained from Cleavage of Multimers

The antimicrobial activity of the cleaved peptides (same samples from Examples 5 and 6) was determined by measuring the dose-dependent inhibition of E. coli growth. The samples were tested for their ability to inhibit the growth of an overnight culture inoculated with E. coli strain BL21 (DE3).

AMP samples were diluted serially into water in 96 well plates. Overnight cultures of E. coli BL21 (DE3) cells were diluted 1:50 into LB broth and 250 µl aliquots were transferred into 96-well plates. Each plate was incubated at 37° C. for one hour and then 50 µl of diluted peptide (or water) were added to each well. Each plate was incubated overnight at 37° C. and then the culture density was determined by measuring the apparent absorbance at 600 nm using a Spectromax Plus plate reader.

The dimer sample obtained after formic acid treatment was found to possess significant antimicrobial activity while the water-treated dimer had no activity.

These experiments clearly indicate that antimicrobial peptides are produced by acid cleavage of the D2A21' concatemeric precursors. However, in order to further demonstrate that the expected D2A21' peptide is indeed the product obtained from the reaction, we analyzed the cleavage products using analytical RP-HPLC, LC/MS and MALDI mass spectrometry techniques. These experiments indicate that bona fide D2A21' is obtained from the cleavage of the bacterially expressed dimer and trimer. We have also used these analytical techniques to demonstrate that D2A21' product is obtained from acid treatment of the insoluble AB4 trimer.

EXAMPLE 8

Expression of AMP Concatemer Polypeptides in P. fluorescens

Concatemeric D2A21' genes (dimers and trimers) were subcloned into the P. fluorescens expression plasmid pMYC1803. The plasmid pMYC1803 is a derivative of pTJS260 (see U.S. Pat. No. 5,169,760 to Wilcox) carrying a regulated tetracycline resistance marker and the replication and mobilization loci from the RSF1010 plasmid. The "TF3" trimer is essentially the same as the "AB4" trimer, although a different expression vector was used for production. See SEQ ID NOs:11 and 12. In addition, we also used a "JP2" dimer, a "16A" trimer, a "21A" trimer, and a "21B" trimer. See SEQ ID NOs:36 and 37 for the 16A trimer, SEQ ID NOs:38 and 39 for the 21A trimer, SEQ ID NOs:40 and 41 for the 21B trimer, and SEQ ID NOs:42 and 43 for the JP2 dimer. P. fluorescens cells harboring the AMP expression plasmids were used to inoculate defined medium, and the resulting cultures were grown and induced for 48 hours after the addition of 0.3 mM IPTG. Aliquots from the culture were harvested at various time points before and after induction; these culture samples were extensively analyzed to characterize cell growth, protein production, inclusion body formation, and plasmid stability.

Expression of a substantial amount of trimeric D2A21' was observed in the induced P. fluorescens cultures, especially from the TF3 trimer clone. However, expression levels of these constructs in P. fluorescens was generally lower than the levels observed in *E. coli*. Lower expression of the dimeric D2A21' construct was more evident in *P. fluorescens*.

Immunoblot analysis of extracts from the induced cultures indicated that some degree of degradation of the dimer (and some limited degradation of the trimeric D2A21' precursors) was occurring in *P. fluorescens* samples. Some degradation of the dimer (and limited degradation of the trimer) was also observed in the *E. coli* extracts. Degradation of the concatemeric precursor could have resulted in the production of some mature, biocidal D2A21' (if the degradation had occurred at or near the Asp-Pro linkage). This could have limited further expression of the concatemer. Noting that the induction time for the *E. coli* BL21 (DE3) expression system (3 hours) is much shorter than the induction interval for *P. fluorescens* (48 hours), this longer induction period for the *P. fluorescens* system could make the system more susceptible to a gradual build-up of toxic D2A21' fragments.

EXAMPLE 9

D2A21 Concatemer Fusions

Examples above clearly indicate that concatemerization of D2A21' AMP decreases the toxicity of the peptide. In *E. coli* and *P. fluorescens*, improved expression of D2A21' precursor was observed as the number of D2A21' subunits in the gene was increased from one to two to three. The trimeric D2A21' polypeptide is expressed to very significant levels in both *E. coli* and *P. fluorescens*. In an attempt to still further increase production levels, we examined the effects on concatemer expression of fusing various protein sequences to the D2A21' trimer.

In particular, we focused on two fusion partners: dihydrofolate reductase (DHFR) from *E. coli* and a haloalkane dehalogenase from *R. rhodocrous*. The dehalogenase protein, for example, was selected because it expresses (by itself) to extremely high levels in *P. fluorescens*. The DHFR carrier polypeptide has a pI of 4.77 and a charge (at neutral pH7) of −10.77. The full-length dehalogenase carrier polypeptide has a pI of 4.95 and a charge (at neutral pH7) of −17.25. The truncated dehalogenase carrier peptide, discussed below, has a pI of 5.31 and a charge (at neutral pH7) of −7.53. These values were calculated using Vector NTi software.

(a) DHFR

Figure 4:
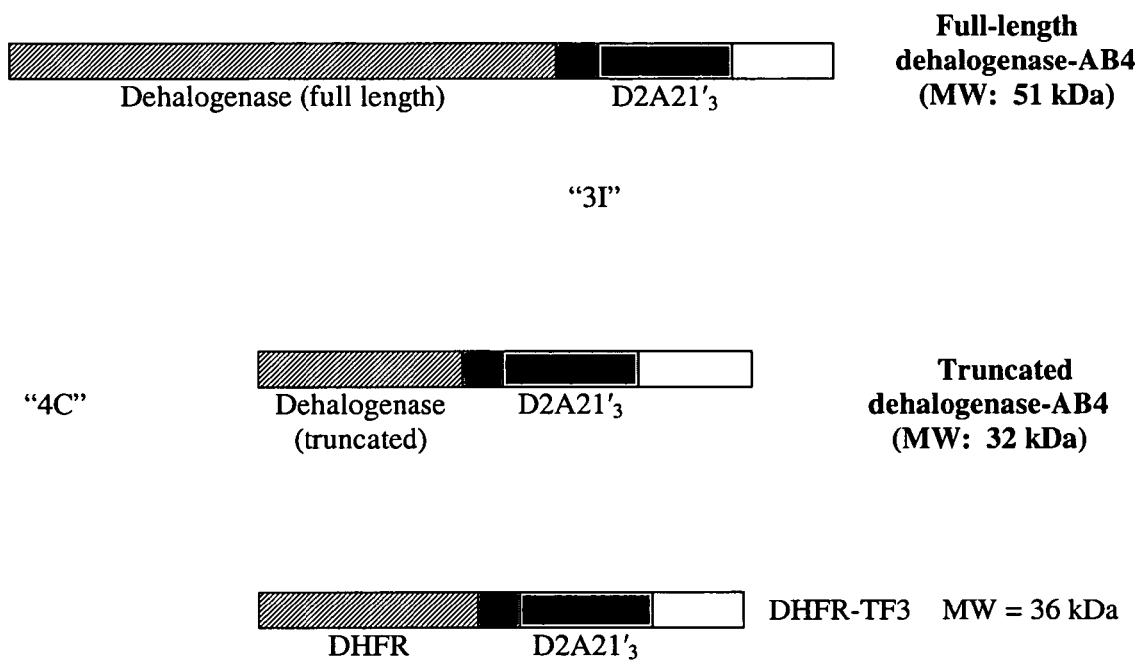
FIG. 4 illustrates fusions/clones discussed in Examples 9 and 10. A central black band depicts a T7 tag epitope for immunoblot detection (part of a leader segment of the AMP multimer). A white band depicts trailer sequences in the multimer.

The DHFR gene (see SEQ ID NOs:20 and 21) was fused to the N termini of TF3 (see SEQ ID NO:11). See SEQ ID NOs:22 and 23. This is illustrated in FIG. 4. N-terminal fusions were also constructed for DHFR/D4E1 trimer (see SEQ ID NOs:24 and 25), tetramer (see SEQ ID NOs:26 and 27), and pentamer (see SEQ ID NOs:28 and 29).

Although no significant induced protein bands were observed by SDS-PAGE analysis, induced protein bands were observed in immunoblots of induced extracts from *P. fluorescens* cells expressing these fusions, particularly for the DHFR-trimeric D2A21' fusions (MW: 34-36 kDa for the DHFR-D2A21 concatemer constructs).

(b) Dehalogenase

The 3I and 4C fusions discussed below are illustrated in FIG. 4.

We created a gene fusion that encodes the dehalogenase (Newman, et al., 1999) protein (see SEQ ID NOs:30 and 31) translationally fused to the N-terminus of the D2A21' trimeric concatemer (AB4) to form the "3I" fusion (see SEQ ID NOs: 32 and 33). In an attempt to increase the ratio of AMP to dehalogenase sequence, another fusion was constructed with a truncated version of the dehalogenase protein containing only the first 123 residues of the protein fused to the N terminus of the AB4 trimer. Incidentally, both the DHFR and dehalogenase proteins are very weakly anionic, and the charged residues of the dehalogenase are evenly distributed across the whole protein. Thus, the 123aa fragment was also only weakly anionic. This construct was called "4C." See SEQ ID NOs:34 and 35. In both cases, the C terminus of the carrier was fused to the N terminus of the multimer.

The dehalogenase-D2A21' fusions were first expressed in *E. coli* using vector pET24-b. After induction, the induced cells were lysed, and the inclusion bodies were harvested (along with other insoluble components such as the cell membranes) by centrifugation. The dehalogenase-D2A21' concatemer fusions expressed very well in *E. coli*. This was especially true for the full length dehalogenase-D2A21' fusions, which accumulated to levels of 300 mg/liter of culture in shake flasks. No dehalogenase-D2A21' protein was detected in the soluble lysate (cytoplasmic) fractions; all of it was found to reside in the insoluble fractions.

EXAMPLE 10

Fusions in *P. fluorescens*

We subcloned both of the dehalogenase/trimeric D2A21' fusions (31 and 4C) into the pMYC1803 plasmid used for expression in *P. fluorescens*. The expression plasmids were electroporated into *P. fluorescens*, and the resulting transformant clones were used to inoculate shake flask cultures containing defined minimal medium. The cultures were grown at 32° C. and induced with IPTG. During the subsequent 48-hour induction period, aliquots were removed from each culture at various time points, and the cells were collected from the medium by centrifugation. The cells were resuspended and lysed in lysis buffer, and the soluble (cytoplasmic) and insoluble fractions were separated by centrifugation and then decanted into separate tubes. The soluble and insoluble fractions were analyzed using SDS-PAGE.

While adequate expression of the AB4 trimer clone was achieved, the 3I (full-length dehalogenase/AB4 trimer) fusion protein was expressed to much higher levels in *E. coli* and *P. fluorescens* than was the AB4 trimer alone. Strong, induced protein bands of appropriate molecular weight are observed in the insoluble fractions of *P. fluorescens* cultures expressing the truncated dehalogenase/D2A21' trimer (4C). Only very small amounts of induced protein were observed in the corresponding soluble fractions from these cells, suggesting that these proteins efficiently form inclusion bodies in *P. fluorescens*. Although considerable amounts of protein accumulated during the first 15 hours of induction, no additional accumulation occured during the next 33 hours.

In *P. fluorescens* as compared to *E. coli*, lower levels of induced protein were observed in the insoluble fraction from cultures expressing full-length dehalogenase-D2A21' trimer, clone 3I. Induced bands were observed in the soluble samples from these cultures, although at a somewhat lower than expected molecular weight (~37 kDa). Extremely high levels of 4C (trimer/truncated fusion) were produced with *P. fluorescens*. These levels exceeded 1 gram per liter in a 20 litre fermentation

EXAMPLE 11

Further Post-Production Processing

Following lysis and initial inclusion body washes, the next step in the post-production processing of the dehalogenase-D2A21' trimer was to solubilize the fusion protein from the inclusion bodies prepared from induced E. coli BL21(DE3) cells. We tested a wide variety of chemical agents including chaotropes such as 8M guanidine HCl or urea and organic solvent mixtures such as 10% butanol, 40% HOAc/40% methanol/20% water, 50% HOAc, 50% HOAC/2% pyridine. The solutions were added to inclusion body preparations, and the suspensions were mixed vigorously. The liquid and solid phases were separated by centrifugation, and the soluble protein concentration in the liquid phase was determined. See Table 3. The dehalogenase-D2A2' trimer fusions were most effectively solubilized by guanidine HCl, urea, acetic acid, and acetic acid/acetonitrile mixture. The solubilization of fusion protein by acetic acid was greatly impeded by small amounts of pyridine. Despite the significant molecular weight difference between the two constructs, the extraction profiles for the full-length and truncated dehalogenase fusions were very similar. The solutions that effectively solubilized the fusion proteins appeared to either denature the proteins (urea and guanidine HCl) or to promote peptide solubility (acetic acid and acetonitrile/acetic acid).

TABLE 3

| Extraction | Full length Dehalogenase version | Truncated dehalogenase version |
|---|---|---|
| 8M guanidine HCl | +++ | +++ |
| 8M urea | ++++ | ++++ |
| 10% butanol | – | – |
| 50% acetic acid | +++ | +++ |
| 50% acetic acid/2% pyridine | – | – |
| 40% acetic acid/40% acetonitrile | +++ | ++ |
| 40% acetic acid/40% methanol | + | + |
| 40% acetic acid/40% ethanol | + | + |
| Water | – | – |

"–" = not solubilized;
"++++" = very effectively solubilized

For the results reported in Table 3, samples containing crude insoluble dehalogenase-D2A21' were treated with each solution, mixed vigorously, and centrifuged. The supernatant was decanted, and the protein concentration was determined.

EXAMPLE 12

Production and Characterization of AMP Product from Concatemers

The guanidine HCl or urea solubilized proteins were acidified with HCl, formic, or acetic acid to pH 1-1.5. The samples were heated to 60° C. for 24-48 hours. Each 24 hours, an aliquot was removed and pH neutralized with TrisCl/NaOH. The acid cleaved products were analyzed using reversed-phase HPLC. A large peak with a retention time of 10.2 minutes was observed after HCl treatment for 24 hours at 60° C. This retention time was identical to that of synthetic D2A21'. The peptide peak at 10.2 minutes had a molecular weight of 3,044.7, which was essentially identical to that expected for D2A21'. A smaller peak at 10.6 minutes retention time was also observed, as well as a significant peak eluting at 9.1 minutes (this peak was not observed for HCl treated samples). These peaks continued to accumulate over time, suggesting that they may be product related. No peaks were observed for the samples from solubilization with urea; this was likely due to an observed precipitation of the samples when they were diluted into mobile phase. The acid-cleavage products contained considerable AMP activity. Collectively the results indicate that hydrolysis of the multimer resulted in the production of biologically active AMP monomers.

Similar results were observed when purified AMP trimer was digested with formic acid at 60° C. The cleaved trimer possessed potent antimicrobial activity. HPLC analysis revealed the presence of a number of chemical species (in addition to the species eluting at 9.1 and 10.6 minutes). We postulated that some or all of these peaks may be derivatives of the D2A21' product. To test this, we analyzed the products of the formic acid digestion of the D2A21' trimer using MALDI-TOF mass spectrometry analysis. A strong peak was observed in the mass spectrum with a mass of 3,045.1; this mass was very close to the expected mass of 3,044.7 for the desired D2A21' product. In addition to this peak, other adduct peaks were observed. A minor peak was observed at a mass value of 2,929.8. This peak probably arose from a D2A21' derivative in which the C-terminal aspartic acid residue was lost (the expected molecular weight of this species (D2A21") was 2,929.6). Although the D2A21" species was present in relatively small amounts in this sample, larger amounts of D2A21" were observed in the product when the cleavage reaction was carried out for a longer time or performed at higher temperatures.

Several other regularly spaced peaks were also observed in the mass spectrum. Subsequent LC-MS analysis of the cleavage products revealed that the D2A21" peak had a slightly higher retention time than the D2A21' parent. These peaks were clustered near the D2A21' and D2A21" peaks. The mass difference between these adduct peaks and the parent peaks was 28 amu. As this mass corresponds to the molecular weight of a formyl adduct, our data suggested that the peptide was formylated by formic acid during the cleavage reaction. This conclusion was supported by the observation that the +28 amu adducts are not observed when the D2A21' trimer is cleaved using acetic acid or dilute HCl.

EXAMPLE 13

Effect of Acid-Cleavage By-Products on Activity

To determine if the loss of the C-terminal aspartic acid residue or formylation of the peptide product affects its antimicrobial activity, highly pure synthetic D2A21' was treated with either formic acid, dilute HCl, or water for 24 hours at 60° C. The samples were concentrated by vacuum drying and then neutralized with Tris/sodium hydroxide prior to analysis by MALDI-TOF mass spectrometry. As with the concatemeric D2A21' precursors, treatment with formic acid caused the formation of both the D2A21" and formylated coproducts while formation of the latter products were not observed in samples treated with dilute HCl. As expected, no by-products of any kind were observed in samples heated in water for 24 hours. Interestingly, comparison of the cleavage by formic and hydrochloric acid using MALDI mass spectrometry and HPLC suggested that the ratio of D2A21' product to D2A21" byproduct was higher for the HCl cleavage reaction products than for the formic acid products. The improved product-to-byproduct ratio was also observed for cleavage reactions using 10% acetic acid.

The C-terminal cleavage and formylation reactions were both highly temperature dependent, as neither the D2A21" nor the formylated peptide products were observed in samples incubated with acid at lower temperatures (4° C.).

In order to measure the effects of these treatments on peptide activity, the antimicrobial activity of each of these samples was measured in duplicate using the standard growth inhibition assay. No significant differences in anti-microbial activity were observed for any of the acid-treated or water treated samples. This result suggested that the formation of the D2A21" or formylated products did not affect the antimicrobial activity of the peptide. However, peptide products cleaved with dilute HCl or acetic acid desirably lack non-naturally occurring by-products that can result from formic acid (and other) hydrolysis of the peptides.

EXAMPLE 14

D4E1 Concatemers/Alternative AMP; Fusions Thereof

Another antimicrobial peptide known as D4E1 was selected to further validate the subject multimer/concatemerization strategies. D4E1 is beta-sheet in structure. The core D4E1 AMP comprises a 17-residue amino acid sequence:

```
                                        (SEQ ID NO:13)
  Phe Lys Leu Arg Ala Lys Ile Lys Val Arg Leu Arg
  Ala Lys Ile Lys Leu
  (FKLRAKIKVRLRAKIKL)
```

DNA sequences were chemically synthesized to construct the multimers of D4E1 for expression in bacteria (see SEQ ID NO:13). D4E1' was cloned into pET24b in the initial approach using methods developed for D2A21' concatemers. Additional residues flanked the core D4E1 sequence, similarly to D2A21'; in fact, this construction contains the addition of an extra Asp-Pro dipeptide on the N-terminus of the D4E1 sequence. The DNA sequences thus encoded a 21-amino-acid peptide comprising the core D4E1 AMP together with an Asp-Pro on both the N and C termini of the core AMP. Acid hydrolysis of concatenated D4E1' peptides are expected to contain single n-terminal pro and c-terminal gly-asp residues, however, just as the D2A21' constructions do.

```
                                        (D4E1, Seq ID:13)
  Asp Pro Phe Lys Leu Arg Ala Lys Ile Lys Val Arg
  Leu Arg Ala Lys Ile Lys Leu Gly Asp Pro
```

Multimers of 2, 3, 4, and 5 were achieved, although no overexpression prevailed when transformed into *E. coli* strain, BL21 (DE3). See SEQ ID NOs:14-17 for the trimer and tetramer sequences. The precursor bacterial product was flanked by a 21-amino-acid sequence harboring a 6×His tag at the C-terminus and 12-amino acid leader sequence containing a T7 tag at the N-terminus. The amino acid sequence of the D4E1 pentamer is:

The DNA sequence that encodes this protein is provided is SEQ ID NO:19.

The charge distribution is given below, where O is nonpolar, polar, hydrophobic or uncharged, + denotes positively charged residues, and – denotes negatively charged residues.
OOOOOOOOOOO+ (Leader sequence from pET24b)
–OO+O+O+O+O+O+O+O+OO–O (D4E1 pentamer)
–OO+O+O+O+O+O+O+O+OO–O
–OO+O+O+O+O+O+O+O+OO–O
–OO+O+O+O+O+O+O+O+OO–O
–OO+O+O+O+O+O+O+O+OO–O
–OOOOOO–+OOOOO–++++++ (trailer sequence)

Concatemers of D4E1 were produced using the aforementioned approach for assembling the D2A21 concatemers.

Directional analyses of the concatemers was tested by digestion with endonucleases and confirmed by agarose gel electrophoresis. Bands representing the concatemers were gel purified. The DNA was subsequently ligated into pET24b (*E. coli*) expression plasmid between its BamH I site using T4 Ligase. The ligation mix was transformed into *E. coli* strain, DH5α library efficient cells and selected for Kanamycin resistance. Kanamycin-resistant strains were single colony isolated. Thereafter, individual colonies were inoculated into LB/Kan media and grown at 37° C. overnight. DNA was extracted from the cells and analyzed by restriction digests. Plasmids containing proper inserts were also analyzed by DNA sequencing.

The trimer, tetramer, and pentamer of D4E1 were then introduced into a *P. fluorescens* expression vector, pMYC1803 using general PCR techniques. Sequence-confirmed concatemers of D4E1 were subcloned into pMYC1803 expression plasmid via PCR using primers to the N- and C-termini of the coding sequence.

PCR products were verified by agarose gel electrophoresis and then digested with the respective enzymes for ligation into the pMYC1803 expression plasmid between its Spe I and Kpn I sites. The expression vector was transformed into bacteria strain JM109 competent cells and plated onto LB and Tetracycline-containing (Tet) agar. Subsequently, individual colonies were inoculated into LB/Tet media and grown up overnight. Cells were then harvested and DNA was extracted and sequenced. Expression levels were determined by SDS-PAGE. Because still higher expression levels were desired. The trimer, tetramer, and pentamer of D4E1 in pMYC1803 were then fused to an N-terminus carrier sequence coding for DHFR.

(a) D4E1-DHFR Fusions in pmyc1803

```
                                                            (SEQ ID NO:18)
Met Ala Ser Met Thr Gly Gly Gln Gln Met Gly Arg Asp Pro Phe Lys Leu Arg      18

Ala Lys Ile Lys Val Arg Leu Arg Ala Lys Ile Lys Leu Gly Asp Pro Asp Pro Phe  37

Lys Leu Arg Ala Lys Ile Lys Val Arg Leu Arg Ala Lys Ile Lys Leu Gly Asp Pro  56

Asp Pro Phe Lys Leu Arg Ala Lys Ile Lys Val Arg Leu Arg Ala Lys Ile Lys Leu  75

Gly Asp Pro Asp Pro Phe Lys Leu Arg Ala Lys Ile Lys Vai Arg Leu Arg Ala Lys  94

Ile Lys Leu Gly Asp Pro Asp Pro Phe Lys Leu Arg Ala Lys Ile Lys Val Arg Leu  113

Arg Ala Lys Ile Lys Leu Gly Asp Pro Asp Pro Asn Ser Ser Val Asp Lys Leu      132

Ala Ala Ala Leu Glu His His His His His His                                  143
```

Confirmed D4E1 pMYC1803 recombinant plasmids were digested with *Nhe*I and *Kpn*I endonucleases to extract D4E1 concatemers; Seq ID NOs:24 and 25 for the trimer fusions and SEQ ID NOs:26 and 27 for the tetramer fusions. DNA fragments were confirmed and quantitated by agarose gel electrophoresis. The DNA was ligated into the *Nhe*I and *Kpn*I sites of an expression vector pMYC1803 containing an existing, upstream sequence encoding DHFR (Dihydrofolate Reductase) between its *Spe*I and *Nhe*I sites. The ligation mix was transformed into JM109 competent cells and plated onto LB/Tet agar. Subsequently, individual colonies were grown in LB/Tet media at 37° C. overnight. Cells were harvested using the procedure previously described; DNAs were subjected to restriction digestions with *Spe*I and *Nhe*I combined, or with *Nhe*I and *Kpn*I combined. The restriction digests were analyzed on agarose gel electrophoresis. However, higher expression levels of the DHFR-D4E1 fusions were still desired.

(b) D4E1 in pMYC 1803 Dehalogenase Fusion Chimers

D4E1 pentamer (SEQ ID NO:18) was fused to the truncated dehalogenase (as in the 4C fusion of SEQ ID NO:34) using general amplification (PCR) and ligation techniques.

The pMYC1803 DHFR D4E1 pentamer was used as a model template for D4E1 in the construction of the pMYC1803 D4E1 pentamer fused to dehalogenase. See SEQ ID NOs:44 and 45. The pMYC1803 Dehalogenase 4C plasmid was used as a DNA template for a truncated dehalogenase (the first 123 amino acids) in the construction of the pMYC1803 D4E1 pentamer fused to dehalogenase. Sense and anti-sense DNA sequences were synthesized that encoded C-terminus dehalogenase and N-terminus T7 tag.

The Sense 5' primer and C-terminus 3' *Kpn*I primer were used to amplify the D4E1 pentamer from the D4E1:DHFR (SEQ ID NOs:28 and 29). The Anti-sense 3' primer along with N-terminus 5' *Spe*I primer were used to amplify the truncated version of dehalogenase from 4C (SEQ ID NOs:34 and 35).

Both PCR products were confirmed by agarose gel electrophoresis. The PCR fragments were quanitated and subsequently combined in equal molar ratio and were subject to restriction with *Nhe*I endonuclease, coded by the PCR primers used, and subsequently ligated. The ligation reaction was used as a template for PCR with 5' *Spe*I primer and 3' *Kpn*I primer to amplify the entire dehalogenase and D4E1 fusion sequence. Subsequently, the PCR was confirmed by agarose gel electrophoresis. The PCR product was then digested with both *Spe*I and *Kpn*I restriction enzymes. The PCR product was ligated into *Pseudomonas fluorescens* strain MB214 expression vector, pMYC1803, between its *Spe*I and *Kpn*I sites. The ligation mix was transformed into JM109 competent cells and plated onto LB/Tet agar. Subsequently, individual colonies were grown in LB/Tet media at 37° C. overnight. Cells were harvested accordingly. Extracted DNA was then used as template for PCR amplification of the dehalogenase fused to the D4E1 sequence. Plasmid DNA confirming the fusion sequence was then subjected to DNA sequencing. See SEQ ID NO:45.

Expression studies in *P. fluorescens* revealed high levels of induced protein and D4E1 monomer peptide after treatment/cleavage with acid. *P. fluorescens* strain MB214 containing this expression plasmid produced at least 1 gram per liter of fermentation broth when grown in a 20 liter fermentor.

The invention claimed is:

1. A method for producing an antimicrobial peptide from 2 to 100 amino acids in length in a microbial host cell, wherein said microbial host cell is a member of the genus *Pseudomonas*, comprising:
   (a) expressing at least one nucleic acid in the microbial host cell, wherein the nucleic acid encodes a fusion polypeptide comprising:
      at least one carrier polypeptide linked by a cleavable linker to at least one peptide multimer, wherein the carrier polypeptide is a hydrolase, wherein the peptide multimer comprises at least two antimicrobial peptides, wherein each antimicrobial peptide has a net positive charge, and each antimicrobial peptide is linked in tandem to another antimicrobial peptide by a cleavage site comprising an Asp-Pro dipeptide, wherein the charge of the carrier polypeptide does not offset the positive charge of the antimicrobial peptide, and wherein the peptide units linked in tandem have the same orientation;
   (b) cleaving the peptide multimer at the cleavage site; and
   (c) isolating the antimicrobial peptide.

2. The method of claim 1, wherein the carrier polypeptide is expressed as at least 2% to 25% of the total cellular protein of the host cell.

3. The method of claim 1, wherein the hydrolase is a glycosidase or dehalogenase.

4. The method of claim 3, wherein the dehalogenase is a haloalkane dehalogenase.

5. The method of claim 4, wherein the dehalogenase is from Rhodococcus rhodochrous TDTM-003.

6. The method of claim 1, wherein the cleavage site is an Asp-Pro dipeptide.

7. The method of claim 6, wherein the multimers are cleaved to produce individual peptide units by an acid.

8. The method of claim 7, wherein the acid is a dilute acid.

9. The method of claim 8, wherein the dilute acid is selected from the group consisting of 0.025 N HCL and 10% acetic acid.

10. The method of claim 1, wherein the individual peptide units upon cleaving contain a Pro amino acid as the first N-terminus amino acid of the peptide unit and an Asp amino acid as the last C-terminus amino acid of the peptide unit.

11. The method of claim 1, wherein the host cell is *Pseudomonas fluorescens*.

12. An isolated microbial cell, wherein said microbial host cell is a member of the genus *Pseudomonas*, comprising at least one nucleic acid, wherein the nucleic acid encodes
   a fusion polypeptide comprising:
   at least one carrier polypeptide linked by a cleavable linker to
   at least one peptide multimer, wherein the peptide multimer comprises
   at least two antimicrobial peptides from 2 to 100 amino acids in length, wherein each antimicrobial peptide has a net positive charge, and each antimicrobial peptide is linked in tandem to another antimicrobial peptide by a cleavage site comprising an Asp-Pro dipeptide, wherein the charge of the carrier polypeptide does not offset the positive charge of the antimicrobial peptide, wherein the peptide units linked in tandem have the same orientation, and wherein the carrier polypeptide is a hydrolase and is expressed as at least 2% to 25% of the total cellular protein of the host cell.

13. The cell of claim 12, wherein the multimer is positively charged.

14. The cell of claim 12, wherein the hydrolase is a glycosidase or dehalogenase.

15. The cell of claim 14, wherein the dehalogenase is a haloalkane dehalogenase.

16. The cell of claim 15, wherein the dehalogenase is from *Rhodococcus rhodochrous* TDTM-003.

17. The cell of claim 12, wherein the cleavage site is an Asp-Pro dipeptide.

18. The cell of claim 12, wherein the multimer contains at least three peptide units.

19. The cell of claim 12, wherein the fusion polypeptide is expressed as an insoluble polypeptide.

20. The cell of claim 12, wherein the fusion polypeptide is expressed at a level of at least 1 g/L.

21. The cell of claim 12, wherein the cell is *Pseudomonas fluorescens*.

22. A *Pseudomonas* based expression vector, comprising:
   at least one nucleic acid encoding a fission polypeptide comprising:
   at least one carrier polypeptide linked by a cleavable linker to at least one peptide multimer, wherein the peptide multimer comprises at least two antimicrobial peptides from 2 to 100 amino acids in length, wherein each antimicrobial peptide has a net positive charge, and each antimicrobial peptide is linked in tandem to another antimicrobial peptide by a cleavage site comprising an Asp-Pro dipeptide, wherein the charge of the carrier polypeptide does not offset the positive charge of the antimicrobial peptide, wherein the peptide units linked in tandem have the same orientation, and wherein the carrier polypeptide is a hydrolase and is expressed as at least 2% to 25% of the total cellular protein of the host cell.

23. The vector of claim 22, wherein the multimer is positively charged.

24. The vector of claim 22, wherein the hydrolase is a glycosidase or dehalogenase.

25. The vector of claim 24, wherein the dehalogenase is a haloalkane dehalogenase.

26. The vector of claim 25, wherein the haloalkane dehalogenase is from *Rhodococcus rhodochrous* TDTM-003.

27. The vector of claim 22, wherein the multimer contains at least three peptide units.

28. The vector of claim 22, wherein the fusion polypeptide is expressed as an insoluble polypeptide.

29. The vector of claim 22, wherein the fusion polypeptide is expressed at a level of at least 300 mg/L.

* * * * *